US010596231B2

(12) United States Patent
Norrman et al.

(10) Patent No.: US 10,596,231 B2
(45) Date of Patent: *Mar. 24, 2020

(54) INSULIN CONTAINING PHARMACEUTICAL COMPOSITIONS

(71) Applicant: Novo Nordisk A/S, Bagsvaerd (DK)

(72) Inventors: Mathias Norrman, Staffanstorp (SE); Susanne Hostrup, Vaerloese (DK); Dorte Bjerre Steensgaard, Maaloev (DK); Holger Martin Strauss, Frederiksberg (DK); Rosa Rebecca Erritzoee Hansen, Koebenhavn (DK); Svend Havelund, Bagsvaerd (DK); Morten Schlein, Vaerloese (DK); Jesper Soendergaard Pedersen, Oelstykke (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,603

(22) Filed: Feb. 20, 2019

(65) Prior Publication Data
US 2019/0183979 A1 Jun. 20, 2019

Related U.S. Application Data

(63) Continuation of application No. 16/023,328, filed on Jun. 29, 2018, now Pat. No. 10,265,385, which is a continuation of application No. 15/843,016, filed on Dec. 15, 2017.

(30) Foreign Application Priority Data

Dec. 16, 2016 (EP) ..................... 16204688

(51) Int. Cl.
A61K 38/28 (2006.01)
A61P 5/48 (2006.01)
A61K 47/02 (2006.01)
A61K 47/10 (2017.01)

(52) U.S. Cl.
CPC .............. A61K 38/28 (2013.01); A61K 47/02 (2013.01); A61K 47/10 (2013.01); A61P 5/48 (2018.01)

(58) Field of Classification Search
CPC ................................................... A61K 38/28
See application file for complete search history.

(56) References Cited

U.S. PATENT DOCUMENTS

| 2,832,685 | A | 4/1958 | Scott |
| 3,528,960 | A | 9/1970 | Haas |
| 3,719,655 | A | 3/1973 | Jackson et al. |
| 3,869,437 | A | 3/1975 | Lindsay et al. |
| 3,950,517 | A | 4/1976 | Lindsay et al. |
| 4,033,941 | A | 7/1977 | Stilz et al. |
| 4,179,337 | A | 12/1979 | Davis et al. |
| 4,462,984 | A | 7/1984 | Mizuno et al. |
| 4,614,730 | A | 9/1986 | Hansen et al. |
| 4,839,341 | A | 6/1989 | Massey et al. |
| 4,849,227 | A | 7/1989 | Cho |
| 5,149,777 | A | 9/1992 | Hansen et al. |
| 5,179,189 | A | 1/1993 | Domb et al. |
| 5,206,219 | A | 4/1993 | Desai |
| 5,266,310 | A | 11/1993 | Mundorf et al. |
| 5,359,030 | A | 10/1994 | Ekwuribe |
| 5,446,020 | A | 8/1995 | Andy et al. |
| 5,478,575 | A | 12/1995 | Miyazaki et al. |
| 5,506,202 | A | 4/1996 | Vertesy et al. |
| 5,506,203 | A | 4/1996 | Backstrom et al. |
| 5,597,796 | A | 1/1997 | Brange |
| 5,621,073 | A | 4/1997 | Dickhardt et al. |
| 5,700,662 | A | 12/1997 | Chance et al. |
| 5,716,927 | A | 2/1998 | Balschmidt et al. |
| 5,898,067 | A | 4/1999 | Balschmidt et al. |
| 5,922,675 | A | 7/1999 | Baker et al. |
| 5,981,489 | A | 11/1999 | Stevenson et al. |
| 6,221,837 | B1 | 4/2001 | Ertl et al. |
| 6,251,856 | B1 | 6/2001 | Markussen et al. |
| 6,475,795 | B1 | 11/2002 | Turley et al. |
| 6,500,645 | B1 | 12/2002 | Kjeldsen et al. |
| 6,746,853 | B1 | 6/2004 | Dahiyat et al. |
| 6,770,625 | B2 | 8/2004 | Soltero et al. |
| 6,858,580 | B2 | 2/2005 | Ekwuribe et al. |
| 6,867,183 | B2 | 3/2005 | Soltero et al. |
| 6,869,930 | B1 | 3/2005 | Havelund et al. |
| 7,030,082 | B2 | 4/2006 | Soltero et al. |
| 7,030,083 | B2 | 4/2006 | Schreiner et al. |
| 7,060,675 | B2 | 6/2006 | Ekwuribe et al. |
| 7,317,000 | B2 | 1/2008 | Hoeg-Jensen et al. |
| 8,691,759 | B2 | 4/2014 | Madsen et al. |
| 8,865,647 | B2 * | 10/2014 | Naver ................. A61K 9/0019 514/6.5 |
| 8,993,516 | B2 | 3/2015 | Weiss |
| 9,018,161 | B2 | 4/2015 | Nielsen et al. |
| 9,045,560 | B2 | 6/2015 | Madsen et al. |
| 9,150,633 | B2 | 10/2015 | Madsen et al. |
| 9,260,503 | B2 | 2/2016 | Hoeg-Jensen et al. |
| 9,481,721 | B2 | 11/2016 | Naver et al. |
| 10,259,856 | B2 | 4/2019 | Madsen et al. |
| 10,265,385 | B2 | 4/2019 | Norrman et al. |

(Continued)

FOREIGN PATENT DOCUMENTS

| CN | 1318416 A | 10/2001 |
| CN | 1390854 A | 1/2003 |

(Continued)

OTHER PUBLICATIONS

Amy S. Rosenberg, "Effects of Protein Aggregates: An Immunologic Perspective," AAPS J, 2006, vol. 8, pp. E501-E507.

(Continued)

Primary Examiner — Gyan Chandra
(74) Attorney, Agent, or Firm — Jianjie Hu

(57) ABSTRACT

The present invention is in the field of pharmaceutical compositions for the treatment of medical conditions relating to diabetes. More specifically the invention provides pharmaceutical compositions comprising a long-acting acylated derivative of a human insulin analogue, and to the medical use of such compositions for basal insulin administration therapy.

12 Claims, 11 Drawing Sheets

(56) References Cited

U.S. PATENT DOCUMENTS

| | | | |
|---|---|---|---|
| 2002/0045731 A1 | 4/2002 | Schaffer et al. |
| 2002/0055496 A1 | 5/2002 | McCoy et al. |
| 2002/0058614 A1 | 5/2002 | Filvaroff et al. |
| 2002/0142955 A1 | 10/2002 | Dubois et al. |
| 2002/0198140 A1 | 12/2002 | Havelund |
| 2003/0027748 A1 | 2/2003 | Ekwuribe et al. |
| 2003/0035775 A1 | 2/2003 | Klibanov |
| 2003/0050228 A1 | 3/2003 | Ekwuribe et al. |
| 2003/0083232 A1 | 5/2003 | Soltero et al. |
| 2003/0104981 A1 | 6/2003 | Mandic |
| 2003/0134294 A1 | 7/2003 | Sandford et al. |
| 2003/0166508 A1 | 9/2003 | Zhang |
| 2003/0228652 A1 | 12/2003 | Radhakrishnan et al. |
| 2004/0038867 A1 | 2/2004 | Still et al. |
| 2004/0097410 A1 | 5/2004 | Zheng et al. |
| 2004/0138101 A1 | 7/2004 | Filvaroff et al. |
| 2004/0198949 A1 | 10/2004 | Ekwuribe et al. |
| 2004/0242460 A1 | 12/2004 | Brader et al. |
| 2004/0254119 A1 | 12/2004 | West et al. |
| 2005/0039235 A1 | 2/2005 | Moloney et al. |
| 2005/0054818 A1 | 3/2005 | Brader et al. |
| 2005/0065066 A1* | 3/2005 | Kaarsholm .......... A61K 31/416 514/6.3 |
| 2005/0232981 A1 | 10/2005 | Ben-Sasson |
| 2005/0276843 A1 | 12/2005 | Quay et al. |
| 2006/0019874 A1 | 1/2006 | Radhakrishnan et al. |
| 2006/0030518 A1 | 2/2006 | Havelund et al. |
| 2006/0182714 A1 | 8/2006 | Behrens et al. |
| 2006/0183668 A1 | 8/2006 | Jonassen et al. |
| 2006/0258561 A1* | 11/2006 | Balschmidt ........ A61K 31/4166 514/6.3 |
| 2007/0054941 A1 | 3/2007 | Biba et al. |
| 2007/0096431 A1 | 5/2007 | Mochizuki et al. |
| 2008/0076705 A1 | 3/2008 | Kodra et al. |
| 2008/0171695 A1 | 7/2008 | Garibay et al. |
| 2008/0200383 A1 | 8/2008 | Jennings et al. |
| 2009/0074882 A1 | 3/2009 | Havelund et al. |
| 2009/0087484 A1 | 4/2009 | Dong et al. |
| 2010/0009898 A1 | 1/2010 | Nielsen et al. |
| 2011/0092419 A1 | 4/2011 | Nelsen et al. |
| 2011/0098440 A1 | 4/2011 | Madsen et al. |
| 2011/0105720 A1 | 5/2011 | Madsen et al. |
| 2011/0230402 A1 | 9/2011 | Johansen et al. |
| 2011/0293714 A1 | 12/2011 | Foger |
| 2011/0294729 A1 | 12/2011 | Stidsen et al. |
| 2012/0196800 A1 | 8/2012 | Naver et al. |
| 2015/0111820 A1 | 4/2015 | Pridal et al. |
| 2015/0126442 A1 | 5/2015 | Naver et al. |
| 2015/0210747 A1 | 7/2015 | Madsen et al. |
| 2015/0210748 A1 | 7/2015 | Madsen et al. |
| 2016/0058840 A1 | 3/2016 | Johansen et al. |
| 2018/0169190 A1 | 6/2018 | Norrman et al. |
| 2019/0112348 A1 | 4/2019 | Madsen et al. |

FOREIGN PATENT DOCUMENTS

| | | |
|---|---|---|
| CN | 1812808 A | 8/2006 |
| CN | 1882356 A | 12/2006 |
| EP | 214826 A2 | 3/1987 |
| EP | 254516 A2 | 1/1988 |
| EP | 265213 A2 | 4/1988 |
| EP | 376156 A2 | 7/1990 |
| EP | 511600 A2 | 11/1992 |
| EP | 544466 A1 | 6/1993 |
| EP | 712861 A2 | 5/1996 |
| EP | 712862 A2 | 5/1996 |
| EP | 837072 A2 | 4/1998 |
| EP | 925792 A2 | 6/1999 |
| EP | 1121144 A1 | 4/2000 |
| EP | 1002547 A1 | 5/2000 |
| EP | 0894095 | 5/2003 |
| GB | 894095 A | 4/1962 |
| GB | 1492997 | 11/1977 |
| GB | 1492997 A | 11/1977 |
| JP | 1254699 | 5/1979 |
| JP | 57-067548 | 4/1982 |
| JP | H01254699 A | 10/1989 |
| JP | H02121929 | 5/1990 |
| JP | H03504240 A | 9/1991 |
| JP | H03-506023 A | 12/1991 |
| JP | H06509796 | 11/1994 |
| JP | H08502490 | 3/1996 |
| JP | H08502492 | 3/1996 |
| JP | H08507066 | 7/1996 |
| JP | H08507078 | 7/1996 |
| JP | H09502867 | 3/1997 |
| JP | H09502867 A | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000/516256 A | 12/2000 |
| JP | 2001-521004 A | 11/2001 |
| JP | 2001-521006 A | 11/2001 |
| JP | 2001-521904 A | 11/2001 |
| JP | 2002-308899 A | 10/2002 |
| JP | 2002-543092 A | 12/2002 |
| JP | 2003-518917 A | 6/2003 |
| JP | 2006-526579 A | 11/2006 |
| JP | 2007-511525 A | 5/2007 |
| JP | 2011121963 A | 6/2011 |
| JP | 2015044875 A | 3/2015 |
| JP | 5749155 B2 | 7/2015 |
| JP | 2016522241 A | 7/2016 |
| RU | 2146139 C1 | 3/2000 |
| RU | 2164520 C2 | 3/2001 |
| RU | 2252782 C2 | 5/2005 |
| WO | 8910937 A1 | 11/1989 |
| WO | 90/01038 A1 | 2/1990 |
| WO | 90/12814 A1 | 11/1990 |
| WO | 91/03935 A1 | 4/1991 |
| WO | 91/12817 A1 | 9/1991 |
| WO | 92/00321 A1 | 1/1992 |
| WO | 92/000322 A1 | 1/1992 |
| WO | 92/01476 A1 | 2/1992 |
| WO | 92/04893 A1 | 4/1992 |
| WO | 92/12999 A1 | 8/1992 |
| WO | 92/012999 A1 | 8/1992 |
| WO | 94/08599 A1 | 4/1994 |
| WO | 94/19020 A1 | 9/1994 |
| WO | 95/07931 A1 | 3/1995 |
| WO | 95/13795 A1 | 5/1995 |
| WO | 95/24183 A1 | 9/1995 |
| WO | 96/15803 A1 | 5/1996 |
| WO | 96/29344 | 9/1996 |
| WO | 96/29344 A1 | 9/1996 |
| WO | 96/37215 A1 | 11/1996 |
| WO | 9702043 A1 | 1/1997 |
| WO | 97/31022 A1 | 8/1997 |
| WO | 98/01473 A1 | 1/1998 |
| WO | 98/02460 A1 | 1/1998 |
| WO | 98/05361 A2 | 2/1998 |
| WO | 9856406 | 12/1998 |
| WO | 99/21573 | 5/1999 |
| WO | 99/21888 A1 | 5/1999 |
| WO | 99/24071 A1 | 5/1999 |
| WO | 99/32116 A1 | 7/1999 |
| WO | 99/65941 A1 | 12/1999 |
| WO | 00/00176 A1 | 1/2000 |
| WO | 00/10541 A1 | 3/2000 |
| WO | 00/23098 A1 | 4/2000 |
| WO | 00/43034 A2 | 7/2000 |
| WO | 0042993 A2 | 7/2000 |
| WO | 00/61178 A1 | 10/2000 |
| WO | 00/64940 A1 | 11/2000 |
| WO | 00/69901 A2 | 11/2000 |
| WO | 00/78302 A1 | 12/2000 |
| WO | 01/01960 A1 | 1/2001 |
| WO | 0100674 A1 | 1/2001 |
| WO | 0143762 | 6/2001 |
| WO | 0152937 | 7/2001 |
| WO | 01/92334 A1 | 12/2001 |
| WO | 02064115 | 8/2002 |

(56) References Cited

FOREIGN PATENT DOCUMENTS

| | | |
|---|---|---|
| WO | 02067969 | 9/2002 |
| WO | 02/094200 | 11/2002 |
| WO | 02/094200 A2 | 11/2002 |
| WO | 02098232 | 12/2002 |
| WO | 02098446 A1 | 12/2002 |
| WO | 03/013573 | 2/2003 |
| WO | 03/022208 A2 | 3/2003 |
| WO | 03/022996 A2 | 3/2003 |
| WO | 03/047493 A2 | 6/2003 |
| WO | 03/048195 A2 | 6/2003 |
| WO | 2003/047493 A2 | 6/2003 |
| WO | 03/053339 A2 | 7/2003 |
| WO | 03/053460 A1 | 7/2003 |
| WO | 03075950 A1 | 9/2003 |
| WO | 03/094951 A1 | 11/2003 |
| WO | 03/094956 A1 | 11/2003 |
| WO | 2003/094951 A1 | 11/2003 |
| WO | 2003/094956 A1 | 11/2003 |
| WO | 04/105790 A1 | 12/2004 |
| WO | 2004/105790 A1 | 12/2004 |
| WO | 05/005477 A2 | 1/2005 |
| WO | 05/012346 A1 | 2/2005 |
| WO | 05/012347 A2 | 2/2005 |
| WO | 05/016312 A1 | 2/2005 |
| WO | 2005/016312 A1 | 2/2005 |
| WO | 2005/027978 A2 | 3/2005 |
| WO | 05/047508 A1 | 5/2005 |
| WO | 2005/047508 A1 | 5/2005 |
| WO | 05/049061 A2 | 6/2005 |
| WO | 05/055976 A2 | 6/2005 |
| WO | 05/058961 A2 | 6/2005 |
| WO | 2005/049061 A2 | 6/2005 |
| WO | 05/092301 A1 | 10/2005 |
| WO | 2005/115441 A2 | 12/2005 |
| WO | 2006005683 A1 | 1/2006 |
| WO | 2006/020580 A2 | 2/2006 |
| WO | 06/023943 A1 | 3/2006 |
| WO | 2006/035418 | 4/2006 |
| WO | 2006060753 A2 | 6/2006 |
| WO | 06/079641 A2 | 8/2006 |
| WO | 06/082204 A1 | 8/2006 |
| WO | 06/082205 A1 | 8/2006 |
| WO | 2006/079641 A2 | 8/2006 |
| WO | 06086856 A1 | 8/2006 |
| WO | 2006/082205 A1 | 8/2006 |
| WO | 2006082245 A1 | 8/2006 |
| WO | 06/097521 A1 | 9/2006 |
| WO | 2006/97521 A1 | 9/2006 |
| WO | 2006/103657 A2 | 10/2006 |
| WO | 2006/125763 | 11/2006 |
| WO | 07/006320 A1 | 1/2007 |
| WO | 2007/006320 A1 | 1/2007 |
| WO | 07/041481 A1 | 4/2007 |
| WO | 07/047948 A2 | 4/2007 |
| WO | 2007/047948 A2 | 4/2007 |
| WO | 07/074133 A2 | 7/2007 |
| WO | 07/081824 A2 | 7/2007 |
| WO | 2007/081824 A2 | 7/2007 |
| WO | 07/096332 A1 | 8/2007 |
| WO | 07/096431 A1 | 8/2007 |
| WO | 2007/096332 A1 | 8/2007 |
| WO | 2007096431 A1 | 8/2007 |
| WO | 07/104737 A1 | 9/2007 |
| WO | 2007104738 A2 | 9/2007 |
| WO | 07/128815 A1 | 11/2007 |
| WO | 07/128817 A2 | 11/2007 |
| WO | 08/15099 A2 | 2/2008 |
| WO | 2008/015099 A2 | 2/2008 |
| WO | 08/034881 A1 | 3/2008 |
| WO | 2008/034881 A1 | 3/2008 |
| WO | 08043033 A2 | 4/2008 |
| WO | 08/132229 A2 | 11/2008 |
| WO | 2008/132224 A2 | 11/2008 |
| WO | 2008/132229 A2 | 11/2008 |
| WO | 08/145730 A1 | 12/2008 |
| WO | 2008/145728 | 12/2008 |
| WO | 2008/145730 A1 | 12/2008 |
| WO | 2008/152106 A1 | 12/2008 |
| WO | 09/010428 A1 | 1/2009 |
| WO | 2009/010428 A1 | 1/2009 |
| WO | 09/022005 A1 | 2/2009 |
| WO | 09/022006 A1 | 2/2009 |
| WO | 2009/021955 A1 | 2/2009 |
| WO | 2009/022005 A1 | 2/2009 |
| WO | 2009/063072 A2 | 5/2009 |
| WO | 2009/112583 A2 | 9/2009 |
| WO | 2009/115469 A1 | 9/2009 |
| WO | 2009152128 A1 | 12/2009 |
| WO | 2010049488 A1 | 5/2010 |
| WO | 2010/066636 A1 | 6/2010 |
| WO | 2010092163 | 8/2010 |
| WO | 2011051486 A2 | 5/2011 |
| WO | 2011/086093 A2 | 7/2011 |
| WO | 2011161124 A1 | 12/2011 |
| WO | 2011161125 A1 | 12/2011 |
| WO | 2012049307 A2 | 4/2012 |
| WO | 12080320 A1 | 6/2012 |
| WO | 2013153000 A2 | 10/2013 |
| WO | 2014202780 | 12/2014 |
| WO | 2015052088 A1 | 4/2015 |
| WO | 2015071368 A1 | 5/2015 |
| WO | 2015131902 A1 | 9/2015 |
| WO | 2015171484 A1 | 11/2015 |
| WO | 2016100042 A1 | 6/2016 |

OTHER PUBLICATIONS

Jonassen et al., "Design of the Novel Protraction Mechanism of Insulin Degludec, an Ultra-Long-Acting Basal Insulin," Pharm Res, 2012, vol. 29, pp. 2104-2114.

Michael F. Dunn, "Zinc-ligand interactions modulate assembly and stability of the insulin hexamer—a review," Biometals, 2005, vol. 18, pp. 295-303.

Bennett, R.G., et al, "Insulin inhibition of the proteasome is dependent on degradation of insulin by insulin-degrading enzyme" Journal of Endocrinology, 2003, vol. 177, pp. 399-405.

Seabright, Paul J et al. Biochemical Journal, "The Characterization of Endosomal Insulin Degradation Intermediates and Their Sequence of Production", 1996, vol. 320, No. 3, pp. 347-956.

Schilling et al., 1991, "Degradation Of Insulin By Trypsin And Alpha Chymotrypsin," Pharmaceutical Research 8 (6):721-727.

Brange et al. ("Design of Novel Insulins with Changed Self-Association and Ligand Binding Properties," GBF Monographs, 1989, 12, 139-144).

Ying-Chi Chu et al. "The A14 Position of Insulin Tolerates Considerable Structural Alterations with Modest Effects on the Biological Behavior of the Hormone," Journal of Protein Chemistry, 1992, vol. 11, Pags 571-577.

Yip, C.C. et al. "Structure and function of Insulin: Preparation and Biological Activity of Guinea Pig DES-B-ASP30, DES-A-ASN21-Insulin." Canadian Journal of Biochemistry, 1976, vol. 54 pp. 866-871.

Stentz, F.B. et al., "Identification of Insulin Intermediates and Sites of Cleavage of Native Insulin by Insulin Protease from Human Fibroblasts," Journal of Biological Chemistry, 1989, vol. 264, No. 34 pp. 20275-20282.

Baker et al., "The Structure of 2Zn Pig Insulin Crystals at 1.5 Å Resolution," Philosophical Transactions of the Royal Society of London, 1988, vol. 319, pp. 369-456.

Ward et al., "Ligand-induced activiation of the insulin receptor: a multi-step process involving structural changes in both the ligand and the receptor," Bioessays, 2009, vol. 31, pp. 422-434.

Seino et al., "Alternative Splicing of Human Insulin Receptor Messenger RNA," Biochemical and Biophysical Research Communications, 1989, vol. 159, pp. 312-316.

Moller et al., "Tissue-Specific Expression of Two Alternatively Spliced Insulin Receptor mRNAs in Man," Molecular Endocrinology, 1989, vol. 3, No. 8, pp. 1263-1269.

(56) References Cited

OTHER PUBLICATIONS

Mosthaf et al., "Functionally Distinct Insulin Receptors Generated by Tissue-Specific Alternative Splicing," The EMBO Journal, 1990, vol. 9, pp. 2409-2413.
Yamaguchi et al., "Functional Properties of Two Naturally Occurring Isoforms of the Human Insulin Receptor in Chinese Hamster Ovary Cells," Endocrinology, 1991, vol. 129, No. 4, Pags 2058-2066.
Yamaguchi et al., "Ligand-Binding Properties of the Two Isoforms of the Human Insulin Receptor," Endocrinology, 1993, vol. 132, No. 3, pp. 1132-1138.
Blundell et al., "Expression on *Escherichia coli* of a chemically synthesized gene for a "mini-C" analog of human proinsulin," Advances in Protein Chemistry, 1972, vol. 26, pp. 279-402.
Pullen et al., "Receptor-binding region of insulin," Nature, 1976, vol. 259, pp. 369-373.
Nakagawa et al., "Role of the COOH-terminal B-chain Domain in Insulin-Receptor Interactions," Journal of Biological Chemistry, 1987, vol. 262, No. 25, pp. 12054-12058.
Mirmira et al., "Importance of the Character and Configuration of Residues B24, B25, and B26 in Insulin-Receptor Interactions," The Journal of Biological Chemistry, 1991, vol. 266, No. 3, pp. 1428-1436.
Xu et al., "Diabetes-Associated Mutations in Insulin: Consecutive Residues in the B Chain Contact Distinct Domains of the Insulin Receptor," Biochemistry, 2004, vol. 43, pp. 8356-8372.
De Meyts et al., "Insulin Interactions with its Receptors: Experimental Evidence for Negative Cooperativity," Biochemical and Biophysical Research Communications, 1973, vol. 55, pp. 154-161.
Kurose et al., "Cross-linking of a B25 Azidophenylalanine Insulin Derivative to the Carboxyl-terminal Region of the ?-Subunit of the Insulin Receptor," Journal of Biological Chemistry, 1994, vol. 269, No. 46, pp. 29190-29197.
Shoelson et al., "BpaB25 Insulins," Journal of Biological Chemistry, 1993, vol. 268, No. 6, pp. 4085-4091.
Zakova et al., "Insulin Analogues with Modifications at Position B26. Divergence of Binding Affinity and Biological Activity," Biochemistry, 2008, vol. 47, pp. 5858-5868.
Fischer et al, "A Shortened Insulin with Full in vitro Potency," Biological Chemistry, 1985, vol. 366, pp. 521-525.
Hua et al., "Receptor binding redefined by a structural switch in a mutant human insulin," Nature, 1991, vol. 354, pp. 238-241.
Ludvigsen et al, "A Structural Switch in a Mutant Insulin Exposes Key Residues for Receptor Binding," Journal of Molecular Biology, 1998, vol. 279, pp. 1-7.
Nakagawa et al., "Importance of Aliphatic Side-Chain Structure at Positions 2 and 3 of Insulin A Chain in Insulin-Receptor Interactions," Biochemistry, 1992, vol. 31, pp. 3204-3214.
Markussen et al., "Single chain des-(B30) insulin," International Journal of Peptide and Protein Research, 1985, vol. 26, No. 1, pp. 70-77.
Shoelson et al., "Three mutant insulins in man," Nature, 1983, vol. 302, pp. 540-543.
Glendorf et al., "Importance of the Solvent-Exposed Residues of the Insulin B Chain ?-Helix for Receptor Binding," Biochemistry, 2008, vol. 47, pp. 4743-4751.
Soos et al., "Monoclonal antibodies reacting with multiple epitopes on the human insulin receptor," Biochemical Journal, 1986, vol. 235, No. 1, pp. 199-208.
Slaaby et al., "Hybrid Receptors Formed by Insulin Receptor (IR) and Insulin-like Growth Factor I Receptor (IGF-IR) Have Low Insulin and High IGF-1 Affinity Irrespective of the IR Splice Variant," Journal of Biological Chemistry, 2006, vol. 281, No. 36, pp. 25869-25874.
Volund, "Application of the Four-Parameter Logisic Model to Bioassay: Comparison with Slope Ratio and Parallel Line Models," Biometrics, 1978, vol. 34, pp. 357-365.
Kabsch, "Automatic Processing of Rotation Diffraction Data from Crystals of Initially Unknown Symmetry and Cell Constants," Journal of Applied Crystallogrpahy, 1993, vol. 26, Pags 795-800.

Vagin et al., "MOLREP: an Automated Program for Molecular Replacement," Journal of Applied Crystallography, 1997, vol. 30, pp. 1022-1025.
Murshudov, "Refinement of Macromolecular Structures by the Maximum-Likelihood Method," Acta Crystallographica, 1997, vol. 53, pp. 240-255.
Emsley et al., "Coot: model-building tools for molecular graphics," Acta Crystallographica, 2004, vol. 60, pp. 2126-2132.
Kjeldsen et al., "Expression of Insulin in Yeast: The Importance of Molecular Adaptation for Secretion and Conversion," Biotechnology and Genetic Engineering Reviews, 2001, vol. 18, pp. 89-121.
Schaffer, "A model for insulin binding to the insulin receptor," European Journal of Biochemistry, 1994, vol. 221, pp. 1127-1132.
Wells, "Additivity of Mutational Effects in Proteins," Biochemistry, 1990, vol. 29, vol. 37, pp. 8509-8517.
Kaarsholm et al., "Engineering Stability of the Insulin Monomer Fold with Application to Structure-Activity Relationships," Biochemistry, 1993, vol. 32, pp. 10773-10778.
Kristensen et al., "Functional Reconsitiution of Insulin Receptor Binding Site from Non-binding Receptor Fragments," Journal of Biological Chemistry, 2002, vol. 277, No. 21, pp. 18340-18345.
Mynarcik et al., "Alanine-scanning Mutagenesis of a C-terminal Ligand Binding Domain of the Insulin Receptor ? Subunit," Journal of Biological Chemistry, 1996, vol. 271, No. 5, pp. 2439-2442.
Whittaker, "Characterization of the Functional Insulin Binding Epitopes of the Full-length Insulin Receptor," Journal of Biological Chemistry, 2005, vol. 280, No. 22, pp. 20932-20936.
Whittaker et al., "Comparison of the Functional Insulin Binding Epitopes of the A and B Isoforms of the Insulin Receptor," Journal of Biological Chemistry, 2002, vol. 277, No. 49, pp. 47380-47384.
Frasca et al., "Insulin Receptor Isoform A, a Newly Recognized High-Affinity Insulin-Like Growth Factor II Receptor in Fetal and Cancel Cells," Molecular and Cellular Biology, 1999, vol. 19, No. 5, pp. 3278-3288.
Kjeldsen et al., "The ligand specificities of the insulin receptor and the insulin-like growth factor I receptor reside in different regions of a common binding site," Proceedings of the National Academy of Sciences of the USA, 1991, vol. 88, No. 10, pp. 4404-4408.
Hinds D K et al. PEGylated insulin in PLGA microparticles. In vivo and in vitro analysis, "Journal of Controlled Release" Year 2005, vol. 104, pp. 447-460.
Poulsen et al., Pharmaceutical Research, "Effect of Ethylenediamine on Chemical Degradation of Insulin Aspart in Pharmaceutical Solutions", 2008, vol. 25, No. 11, pp. 2534-2544.
Prasad et al., Journal of Steroid Biochemistry, "Solid-Phase Reagents for the Isolation and Protection of Carbonyl Compounds", 1983, vol. 18, No. 3, pp. 257-261.
Non-Final Office Action dated Jul. 12, 2010 in U.S. Appl. No. 12/560,833, filed Sep. 16, 2009 by Jonassen et al.
Notice of Abandonment dated Jul. 12, 2010 in U.S. Appl. No. 11/814,374, filed Jan. 29, 2008 by Garibay et al.
Non-Final Office Action dated Nov. 17, 2009 in U.S. Appl. No. 11/814,374, filed Jan. 29, 2008 by Garibay et al.
Non-Final Office Action dated Apr. 17, 2009 in U.S. Appl. No. 11/814,374, filed Jan. 29, 2008 by Garibay et al.
Non-Final Office Action dated Sep. 24, 2010 in U.S. Appl. No. 11/814,019, filed Oct. 4, 2007 by Kodra et al.
Advisory Action dated Jul. 23, 2010 in U.S. Appl. No. 11/814,019, filed Oct. 4, 2007 by Kodra et al.
Final Office Action dated Feb. 1, 2010 in U.S. Appl. No. 11/814,019, filed Oct. 4, 2007 by Kodra et al.
Non-Final Office Action dated Jun. 18, 2009 in U.S. Appl. No. 11/814,019, filed Oct. 4, 2007 by Kodra et al.
Notice of Allowance dated Sep. 8, 2009 in U.S. Appl. No. 11/343,005, filed Jan. 30, 2006 by Jonassen et al.
Advisory Action dated Mar. 20, 2009 in U.S. Appl. No. 11/343,005, filed Jan. 30, 2006 by Jonassen et al.
Final Office Action dated Dec. 24, 2008 in U.S. Appl. No. 11/343,005, filed Jan. 30, 2006 by Jonassen et al.
Non-Final Office Action dated Jul. 11, 2008 in U.S. Appl. No. 11/343,005 filed Jan. 30, 2006 by Jonassen et al.
Notice of Allowance dated Feb. 6, 2007 in U.S. Appl. No. 10/620,651, filed Jul. 16, 2003 by Markussen et al.

(56) References Cited

OTHER PUBLICATIONS

Non-Final Office Action dated Jun. 27, 2006 in U.S. Appl. No. 10/620,651, filed Jul. 16, 2003 by Markussen et al.
Notice of Allowance dated Apr. 9, 2003 in U.S. Appl. No. 09/861,687, filed May 21, 2001 by Markussen et al.
Non-Final Office Action dated Sep. 27, 2002 in U.S. Appl. No. 09/861,687, filed May 21, 2001 by Markussen et al.
Notice of Allowance dated Feb. 22, 2001 in U.S. Appl. No. 08/932,082, filed Sep. 17, 1997 by Markussen et al.
Final Office Action dated Oct. 20, 2000 in U.S. Appl. No. 08/932,082, filed Sep. 17, 1997 by Markussen et al.
Non-Final Office Action dated May 23, 2000 in U.S. Appl. No. 08/932,082, filed Sep. 17, 1997 by Markussen et al.
Final Office Action dated Jun. 17, 1999 in U.S. Appl. No. 08/932,082, filed Sep. 17, 1997 by Markussen et al.
Non-Final Office Action dated Sep. 23, 2008 in U.S. Appl. No. 08/932,082, filed Sep. 17, 1997 by Markussen et al.
Notice of Abandonment dated Mar. 12, 1998 in U.S. Appl. No. 08/448,210, filed May 23, 1995 by Markussen et al.
Notice of Allowance dated May 27, 1997 in U.S. Appl. No. 08/448,210, filed May 23, 1995 by Markussen et al.
Non-Final Office Action dated May 30, 1996 in U.S. Appl. No. 08/448,210, filed May 23, 1995 by Markussen et al.
Toorisaka, Eiichi et al, Membrane "Emulsion-Based Drug Delivery Systems", 2004, vol. 29, No. 2, pp. 98-104.
Bekerman, Tania et al, Journal of Pharmaceutical Sciences, "Cyclosporin Nanoparticulate Liposheres for Oral Administration", 2004, vol. 93, No. 5, pp. 1264-1270.
Klibanov et al, "Biotechnology and Bioengineering on Protein Solubility in Organic Solvents" 1994 vol. 44 pp. 140-145.
Toorisaka, et al., "Emulsion Based Drug Delivery Systems," Membrane, 2004, vol. 29, No. 2, pp. 98-104.
Chu et al., 1992, "The A14 Position Of Insulin Tolesrates Considerable Structural Alterations With Modest Effects On The Biological Behavior Of The Hormone," Journal Of Protein Chemistry 11(5):571-577.
Iwamoto, Yasuhiko, 2000, "New Insulin Formulation," Annual Review Increation and Metabolism, pp. 46-53.
Jonassen et al., 2006, "Biochemical and Physiological Properties of a Novel Series of Long-Acting Insulin Analogs Obtained by Acylation with Cholic Acid Derivatives", Pharmaceutical Research, vol. 23, No. 1, pp. 49-55.
Kurtz et al., 1983, "Circulating IgG Antibody to Protamine in Patients Treated with Protamine-Insulins," Diabetologia 25(4):322-324.
Samuel et al., 1978, "Studies On The Immunogenicity Of Protamines In Humans And experimental Animals By Means Of A Micro-Complement Fixation Test," Clinical Experminental Immunology 33:252-260.
Seabright et al., 1996, "The Characterization Of Endosomal Insulin Degradation Intermediates And Their Sequence Of Production," Biochemical Journal 320(3):947-956.
Stentz et al., 1989, "Identification Of Insulin Intermediates And Sites Of Cleavage Of Native Insulin By Insulin Protease From Human Fibroblasts," Journal of Biological Chemistry 264(34):20275-20285.
Teagarden DL, Baker DS, European Journal of Pharmaceutical Sceiences, Practical Aspects of Lyophilization using non-aqueours co-solvent systems, 2002, vol. 15, No. 2, pp. 115-133.
Level of Protein Structure, Exemplified by Insulin. http://www.biotopics.co.uk/as/insulinproteinstructure.html, accessed Dec. 13, 2012.
Ichikawa, J. Pharm Pharmacol., May 1980; vol. 32(5); pp. 314-318 (abstract only).
Brange et al (1992) "Chemical Stability of Insulin. 2. Formation of Higher Molecular Weight Transformation Products During Storage of Pharmaceutical Preparations" Pharmaceutical Research vol. 9: 727-734.
Kudvu and Basu, "Ultra-Long-Acting Insulins for a Lifestyle-Related Pandemic," Lancet, 2011, vol. 377, pp. 880-881.

American Diabetes Association, "Diagnosis and Classification of Diabetes Mellitus," Diabetes Care, 2010, vol. 33, Supp 1, pp. S62-S69.
Bethel and Feinglos (Bethel), "Basal Insulin Therapy in Type 2 Diabetes," J Am Board Fam Med, 2005, vol. 18, No. 3, pp. 199-204 (printed as pp. 1-7).
Bajaj et al., "Coypu Insulin: Primary Structure, Conformation and Biological Properties of a Hystricomorph Rodent Insulin", Journal of Biochemistry, 1986, vol. 238, pp. 345-351.
Spoden M et al. International Journal of Peptide and Protein. "Structure-Function Relationships of DES-(B26-B30)-Insulin." 1995. vol. 46(3-4). pp. 221-227.
Chen, Y et al. Journal of Biological Chemistry. "In Vitro Refolding/Unfolding Pathways of Amphioxus Insulin-Like Peptide Implications for Folding Behavior of Insulin Family Proteins." 2004. vol. 279(53). pp. 55224-55233.
Smith, L.E, "Accession: P01337 1 [gi: 32172038] & Accession: P01337 2 [gi: 32172039], Definition: [Segment 1 of 2] Insulin-1 & [Segment 2 of 2] Insulin-1", NCBI Entrez Protein [online]; Mar. 21, 2006 uploaded, NCBI, [retrieved on Sep. 11, 2013], Retrieved from the internet:http://www.ncbi.nlm.nih.gov/protein/32172037?sat=34 &satkey=10044352.
Aminlari et al., 1977, "Protein Dispersibility Of Spray-Dried Whole Soybean Milk Base: Effect Of Processing Variables," Journal of Food Science 42(4):985-988.
Bekerman et al., 2004, "Cyclosporin Nanoparticulate Liposheres For Oral Administration," Journal of Pharmaceutical Sciences 93(5)1264-1270.
Bennett et al., 2003, "Insulin Inhibition Of The Proteasome Is Dependent On Degradation Of Insulin By Insulin-Degrading Enzyme," Journal of Endocrinology 177:399-405.
Bhatnagar et al., 2006, "Molecular Variants And Derivatives Of Insulin For Improved Glycemic Control In Diabetes," Progress in Biophysics and Molecular Biology 91(3):199-228.
Chin et al., 1994, "Communication to the Editor: On Protein Solubility in Organic Solvents," Biotechnology and Bioengineering 44:140-145.
Foster et al., 1995, "Powder Characteristics Of Proteins Spray-Dried From Different Spray-Driers," Drug Development and Industrial Pharmacy 21(15):1705-1723.
Hartmann et al., 1992, "Comparison Of Subcutaneously Administered Soluble Insulin And Des-(B26-B30)-Insulin-B25-Amide In Rabbit, Pig And Healthy Man," Diabetes Research and Clinical Practice 16(3):175-181.
Hashimoto et al., 1989, "Synthesis of Palmitoyl Derivatives of Insulin and Their Biological Activities" Pharmaceutical Research 6(2):171-176.
Havelund et al., 2004, "The Mechanism Of Protraction Of Insulin Detemir, a Long-Acting, Acylated Analog of Human Insulin" Pharmaceutical Research 21(8):1498-1504.
Hinds et al., 2000, "Synthesis And Characterization Of Poly(Ethylene Glycol)-Insulin Conjugates," Bioconjugate Chemistry 11(2):195-201.
Hinds et al., 2002, "Effects Of Peg Conjugation On Insulin Properties," Advanced Drug Delivery Reviews 54 (4):505-530.
Iwamoto, 2000, "New Insulin Formulation," Annual Review Endocrine Metabolism pp. 46-53.
Jonassen et al., 2006, "Synthesis of Palmitoyl Derivatives of Insulin and Their Biological Activities," Pharmaceutical Research 23(1):49-55.
Kochendoerfer et al., 2003, "Design And Chemical Synthesis Of A Homogenous Polymer-Modified Erythropoiesis Protein," Science 299:884-887.
Kurtz et al., 1983, "Circulating IgG Antibody to Protamine in Patients Treated with Protamine-Insulins," Diabetologia 25(2):322-324.
Markussen et al., 1987, "Soluble, Prolonged-Acting Insulin Derivatives. I. Degree Of Protraction, Crystallizability Of Insulins Substituted In The . . . " Protein Engineering 1(3):205-213.
Markussen et al., 1988, "Soluble, Prolonged-Acting Insulin Derivatives. III Degree Of Protraction, Crystallizability And Chemical Stability Of Insulins Substituted In Positions A21, B13, B23, B27 and B30," Protein Engineering 2 (2):157-166.

(56) References Cited

OTHER PUBLICATIONS

Muranishi et al., 1992, "Trials Of Lipid Modification Of Peptide Hormones For Intestinal Delivery," Journal Of Controlled Release 19:179-188.
Samuel et al., 1978, "Studies On The Immunogenicity Of Protamines In Humans Andexperimental Animals By Means Of A Micro-Complement Fixation Test," Clinical Experminemtal Immunology 33:252-260.
Schlichtkrull et al., 1956, "Insulin Crystals," Acta Chemica Scandinavica 10(9):1455-1458.
Toorisaka et al., 2004, "Emulsion-Based Drug Delivery Systems," Membrane 29(2):98-104 Abstract.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
L. Schaffer et al ,A novel high-affinity peptide antagonist to the insulin receptor.Journal: Biochemical and Biophysical Research Communications, Year 2008, vol. 376 , pp. 380-383.
L. Schaffer et al, Assembly of high-affinity insulin receptor agonists and antagonists from peptide building blocks, Journal :Proceedings of the National Academy of Sciences of the United States of America, Year 2003, vol. 100, pp. 4435-4439.
Riebel, U. et al,Equivalent In Vivo Biological Activity of Insulin Analogues and Human Insulin Despite Different In Vitro Potencies, Journal :Diabetes, Year 1990,vol. 39, pp. 1033-1039.
Hinds, K D et al. Advanced Drugs Delivery Reviews. "Effects of Peg Conjugation on Insulin Properties." 2002. vol. 54. pp. 505-530.
Chu Ying-Chi et al. Journal of Protein Chemistry. "The A14 Position of Insulin Tolesrates Considerable Structural Alterations With Modest Effects on the Biological Behavior of the Hormone." 1992. vol. 11(5). pp. 571-577.
Database Geneseq [Online] May 7, 1992 (May 7, 1992), "Modified human proinsulin with Gln A13 and Asp B17.", retrieved from EBI accession No. GSP:AAR20702 Database accession No. AAR20702.
Definition of hydrophobic and hydrophilic, Amino Acids, NJMS Department of Biochemistry and Molecular Biology. (http://njms2.umdnj.edu/biochweb/education/bioweb/PreK/AminoAcids.htm), accessed Dec. 16, 2014.
Hydrophobic Amino Acids, Molecular Cell Biology 6th edition (2008, W.H. Freeman and company) http://www.bio.miami.edu/tom/courses/protected/MCB6/ch02/2-14_part_1.jpg.
The online Medical dictionary year 2005 Website:http://cancerweb.ncl.ac.uklomd/about.html, 5 pages, Jul. 7, 2005.
Biopharmaceutics and Pharmacokinetics, Edited by Li Xiaotian, Zhao Yongxing, Zhengzhou: Zhengzhou University Press, 2006, pp. 67-71.
Joseph A. Affholter et al., "Identification of Residues in the Insulin Molecule Important for Binding to Insulin-Degrading Enzyme," Biochemistry, 1990, vol. 29, No. 33, pp. 7727-7733.
Kudvu & Basu, "Ultra-Long-Acting Insulins for a Lifestyle-Related Pandemic," Lancet, 2011, vol. 377, pp. 880-881.
Havelund et al., "The Mechanism of Protraction of Insulin Detemir, a Long-Acting, Acylated Analog of Human Insulin," Pharmaceutical Research, 2004, vol. 21, No. 8, pp. 1498-1504.
Chu, Ying-Chi et al., "The A14 Position of Insuling Tolerates Considerable . . . " J. Protein Chem., vol. 11(5), pp. 571-577 (1992).
Huang Tao, "Preparation and MALDI-TOF-MS Analysis of the . . . " Chemical Research & Application, vol. 18(7), pp. 834-836 (2006).
Authier F et al. "Uptake and Metabolic Fate of [HisA8,HisB4,GluB10,HisB27]insulin in rat liver in vivo." Biochemistry Journal. 1998. vol. 332 pp. 421-430.
Yang, S.Z. et al. "Relationship between insulin A chain regions and insulin biological activities." World J Gastroentero. 2000 vol. 6(3): 371-373.
Brems, D.N. et al. "Improved insulin stability through amino acid substitution" Protein Engineering. 1992 vol. 5(6): 519-525.
Bhatnagar S et al. Molecular variants and derivatives of insulin for improved glycemic control in diabetes, "Progress in Biophysics and Molecular Biology" Year 2006, vol. 91, No. 3, pp. 199-228, XP027932180.
David R.Owens New Horizons—Alternative Routes for Insulin Therapy, "Nature Reviews Drug Discovery" year 2002, vol. 1, No. 7, pp. 529-540, XP002682141.
R. Murray et al., Human Biochemistry in 2 Volumes, vol. 1, Moscow, "Mir", 1993, p. 384.
Chang-Cheng You et al., "Contrasting Effects of Exterior and Interior Hydrophobic Moieties in the Complexation of Amino Acid Functionalized Gold Clusters with Alpha-Chymotrypsin," Organic Letters, 2005, vol. 7, No. 25, pp. 5685-5688.

* cited by examiner

Fig. 1A
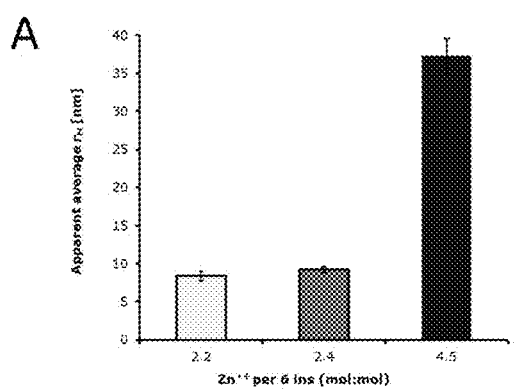
Fig. 1B
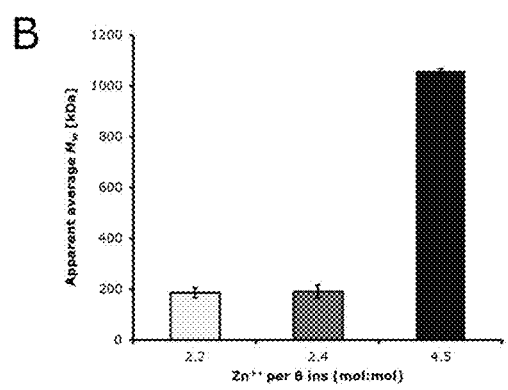
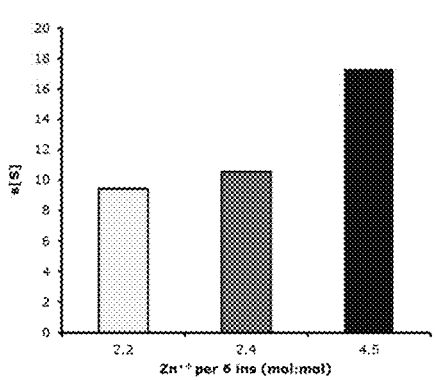
Fig. 1C

INSULIN CONTAINING PHARMACEUTICAL COMPOSITIONS

CROSS-REFERENCE TO RELATED APPLICATIONS

This application is a continuation of U.S. application Ser. No. 16/023,328, filed Jun. 29, 2018, which is a continuation of U.S. application Ser. No. 15/843,016, filed Dec. 15, 2017, which claims priority to European Patent Application 16204688.2, filed Dec. 16, 2016; the contents of which are incorporated herein by reference.

TECHNICAL FIELD

The present invention is in the field of pharmaceutical compositions for the treatment of medical conditions relating to diabetes. More specifically the invention provides pharmaceutical compositions comprising a long-acting acylated derivative of a human insulin analogue, and to the medical use of such compositions for basal insulin administration therapy.

BACKGROUND ART

The primary objective of insulin therapy in the treatment of metabolic disorders is to produce sustained near-normal glycemia by replacing or supplementing endogenous insulin secretion in as physiological a manner as possible, postprandially as well as between meals and overnight. Separating basal and meal-related (bolus) insulin requirements represents a systematic approach to subcutaneous insulin therapy.

The most relevant pharmacological characteristics of any given insulin—onset of action, peak effect profile, duration of action, etc.—are largely determined by its absorption kinetics from the subcutaneous injection site into the systemic circulation.

Non-covalent zinc mediated oligomerisation is a well-described property of insulin products. Under physiological pH, human insulin is soluble but has a tendency to self-associate into well-defined hexamers (i.e. a unit of six insulin molecules), by coordination of two zinc ions ($Zn^{++}$) to high affinity (B10His) binding sites. It is also well-known that phenolic ligands, especially phenol, bind specifically to the insulin hexamer and promote R-state hexamer formation. Upon injection, phenolic ligands diffuses quickly from the injection site. In the absence of phenol at the injection site, the conformation and size of the insulin oligomer may change, as well as the viscosity of the insulin-containing solution, contributing to a prolonged action profile.

Jonassen et al, Pharm. Res. 2012 29 2104-2114 describe the protraction mechanism of insulin degludec, an insulin derivative with acylated fatty di-acid chain for once-daily administration, and describe the correlation between high zinc concentration and the protraction. WO 2009/115469 describes various long-acting insulin derivatives with acylated fatty di-acid chains. WO 2013/153000 describes the formulation of those long-acting insulin derivatives for subcutaneous administration, which contains high level of zinc (no less than 3.5 $Zn^{++}$/six moles of insulin derivatives). It was designed in order to obtain the prolonged duration of action commensurate with a once-weekly administration profile. High content of $Zn^{++}$ in the formulations described in WO 2009/115469 lead to a prolonged PK profile.

WO 2009/063072 discloses pharmaceutical compositions for parenteral administration comprising a basal insulin derivative (e.g. degludec) and a GLP-1 derivative (e.g, liraglutid). Because liraglutide monomer binds with zinc to form di-heptmer, zinc level higher than the degludec mono formulation is necessary in the combo formulation, to achieve comparable PK profile of degludec, and achieve acceptable physical stability.

SUMMARY OF THE INVENTION

According to the present invention a new formulation of the long-acting insulin derivatives has been developed, which is capable of promoting a conformational state and oligomerisation pattern more closely resembling that of human insulin, i.e. hexamers, especially R6 hexamers.

In another aspect, the invention provides a pharmaceutical composition comprising a selected long-acting insulin derivative in a unique combination of excipients carefully formulated in order to reduce formation of oligomers at the injection site, while still showing PK/PD properties suited for a once-weekly administration.

In another aspect, the invention provides a pharmaceutical composition with decreased viscosity upon injection and accordingly decreased propensity to create any discomfort upon injection.

In another aspect, the invention provides a pharmaceutical composition with improved stability.

In another aspect, the invention provides a pharmaceutical composition for use as a medicament for the treatment of a metabolic disorder.

Other objects of the invention will be apparent to the person skilled in the art from the following detailed description and examples.

DETAILED DISCLOSURE OF THE INVENTION

In its first aspect the invention provides pharmaceutical composition comprising an insulin derivative selected from the group consisting of A14E, B16H, B25H, B29K(($N^{\varepsilon}$-Eicosanedioyl-γGlu-[2-(2-{2-[2-(2-aminoethoxy)-ethoxy]acetylamino}ethoxy)ethoxy]acetyl)), desB30 human insulin; (Compound 1);

A14E, B16H, B25H, B29K($N^{\varepsilon}$-Hexadecandioyl-γGlu), desB30 human insulin (Compound 2);

A14E, B16H, B25H, B29K($N^{\varepsilon}$-Eicosanedioyl-γGlu), desB30 human insulin (Compound 3); and A14E, B25H, desB27, B29K($N^{\varepsilon}$-Octadecandioyl-γGlu), desB30 human insulin (Compound 4); and further comprising of from about 1 to about 2% (weight/weight) of glycerol; of from about 45 to about 75 mM of phenol; of from about 0 to about 19 mM of m-cresol; of from about 1.5 to about 2.5 moles of zinc ions per six moles of said insulin derivative; not more than about 75 mM of sodium chloride; and having a pH value in the range of from 7.2 to 8.0.

In anther aspect, the invention provides pharmaceutical compositions further comprising an insulinotropic GLP-1 compound, and in particular the insulinotropic GLP-1 compound known as semaglutide.

Semaglutide may be bescribed by the structure Aib8, Lys26(OEG-OEG-gamma-Glu-C18-diacid),Arg34)GLP-1 H(7-37)-OH, which may also be designated as (N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy)-acetyl][Aib8,Arg34]GLP-1-(7-37), c.f. disclosure in WO 2006/097537.

The present invention may be further characterised by reference to one or more of the following features or embodiments:

1. A pharmaceutical composition of the invention comprising an insulin derivative, which is A14E, B16H, B25H, B29K((N$^\varepsilon$-Eicosanedioyl-γGlu-[2-(2-{2-[2-(2-aminoethoxy)ethoxy]acetylamino}ethoxy)ethoxy]acetyl)), desB30 human insulin (Compound 1).

2. A pharmaceutical composition of the invention comprising an insulin derivative, which is A14E, B16H, B25H, B29K(N$^\varepsilon$-Hexadecandioyl-γGlu), desB30 human insulin (Compound 2).

3. A pharmaceutical composition of the invention comprising an insulin derivative, which is A14E, B16H, B25H, B29K(N$^\varepsilon$-Eicosanedioyl-γGlu), desB30 human insulin (Compound 3).

4. A pharmaceutical composition of the invention comprising an insulin derivative, which is A14E, B25H, desB27, B29K(N$^\varepsilon$-Octadecandioyl-γGlu), desB30 human insulin (Compound 4).

5. The pharmaceutical composition of the previous embodiments, wherein the insulin derivative is in the range of from about 3.5 to about 5.0 mM.

6. The pharmaceutical composition of the previous embodiments, wherein the insulin derivative is in the range of from about 4.0 to about 4.5 mM.

7. The pharmaceutical composition of the previous embodiments, wherein the insulin derivative is about 4.2 mM.

8. The pharmaceutical composition of the previous embodiments, comprising of from about 1 to about 2% (weight/weight) of glycerol.

9. The pharmaceutical composition of the previous embodiments, comprising of from about 1.4 to about 1.8% (weight/weight) of glycerol.

10. The pharmaceutical composition of the previous embodiments, comprising about 1.5% or 1.6% (weight/weight) of glycerol.

11. The pharmaceutical composition of the previous embodiments, comprising of from about 45 to about 75 mM of phenol.

12. The pharmaceutical composition of previous embodiments, comprising of from about 50 to about 70 mM of phenol.

13. The pharmaceutical composition of previous embodiments, comprising of from about 55 to about 65 mM of phenol.

14. The pharmaceutical composition of the previous embodiments, comprising about 50, 51, 52, 53, 54, 55, 56, 57, 58, 59, 60, 61, 62, 63, 64, 65, 66, 67, 68, 69, or 70 mM of phenol.

15. The pharmaceutical composition of the previous embodiments, comprising of from about 0 to about 19 mM of m-cresol.

16. The pharmaceutical composition of the previous embodiments, comprising 0 mM, 1 mM, 2 mM, 3 mM, 4 mM of m-cresol.

17. The pharmaceutical composition of the previous embodiments, comprising of from about 0 to about 15 mM of m-cresol.

18. The pharmaceutical composition of the previous embodiments, comprising about 5 mM, 6 mM, 7 mM, 8 mM, 9 mM, 10 mM, 11 mM, 12 mM, 13 mM, 14 mM, 15 mM, 16 mM, 17 mM, 18 mM or 19 mM of m-cresol.

19. The pharmaceutical composition of the previous embodiments, comprising of from about 1.5 to about 2.5 moles of zinc ions per six moles of insulin derivative.

20. The pharmaceutical composition of the previous embodiments, comprising of from about 2.0 to about 2.4 moles of zinc ions per six moles of insulin derivative.

21. The pharmaceutical composition of the previous embodiments, comprising about 2.0 or 2.1 moles of zinc ions per six moles of insulin derivative.

22. The pharmaceutical composition of the previous embodiments, comprising about 2.2 or 2.3 moles of zinc ions per six moles of insulin derivative.

23. The pharmaceutical composition of the previous embodiments, comprising about 2.4 or 2.5 moles of zinc ions per six moles of insulin derivative.

24. The pharmaceutical composition of the previous embodiments, comprising less than about 75 mM of sodium chloride.

25. The pharmaceutical composition of the previous embodiments, comprising of from about 5 to about 50 mM of sodium chloride.

26. The pharmaceutical composition of the previous embodiments, comprising of from about 10 to about 25 mM of sodium chloride.

27. The pharmaceutical composition of the previous embodiments, comprising of from about 15 to about 25 mM of sodium chloride.

28. The pharmaceutical composition of the previous embodiments, comprising about 20 mM, 50 mM or 75 mM of sodium chloride.

29. The pharmaceutical composition of the previous embodiments, which has a pH value in the range of from 7.2 to 8.0.

30. The pharmaceutical composition of the previous embodiments, which has a pH value in the range of from 7.2 to 7.6.

31. The pharmaceutical composition of the previous embodiments, which has a pH value about 7.2, 7.3, 7.4, 7.5, 7.6, 7.7, 7.8, or 7.9.

32. The pharmaceutical composition of the previous embodiments, comprising
of from about 4.0 to about 4.5 mM of insulin derivative;
of from about 1 to about 2% (weight/weight) of glycerol;
of from about 50 to about 70 mM of phenol;
of from about 0 to about 15 mM of m-cresol;
of from about 2.0 to about 2.5 moles of zinc ions per six moles of insulin derivative;
less than about 50 mM of sodium chloride; and
is having a pH value in the range of from 7.2 to 7.6.

33. The pharmaceutical composition of the previous embodiments, comprising
of about 4.2 mM of insulin derivative;
of about 1.5% (weight/weight) of glycerol;
of about 60 mM of phenol;
of about 0 mM of m-cresol;
of about 2.0 moles of zinc ions per six moles of insulin derivative;
of about 20 mM of sodium chloride; and
is having a pH value of about 7.4.

34. The pharmaceutical composition of previous embodiments, comprising
of about 4.2 mM of insulin derivative;
of about 1.5% (weight/weight) of glycerol;
of about 60 mM of phenol;
of about 10 mM of m-cresol;
of about 2.0 moles of zinc ions per six moles of insulin derivative;
of about 20 mM of sodium chloride; and
is having a pH value of about 7.4.

35. The pharmaceutical composition of the previous embodiments, comprising
of about 4.2 mM of insulin derivative;
of about 1.5% (weight/weight) of glycerol;

of about 60 mM of phenol;
of about 0 mM of m-cresol;
of about 2.2 moles of zinc ions per six moles of insulin derivative;
of about 20 mM of sodium chloride; and
is having a pH value of about 7.4.

36. The pharmaceutical composition previous embodiments, comprising
of about 4.2 mM of insulin derivative;
of about 1.5% (weight/weight) of glycerol;
of about 60 mM of phenol;
of about 10 mM of m-cresol;
of about 2.2 moles of zinc ions per six moles of insulin derivative;
of about 20 mM of sodium chloride; and
is having a pH value of about 7.4.

37. The pharmaceutical composition of previous embodiments, comprising
of about 4.2 mM of insulin derivative;
of about 1.5% (weight/weight) of glycerol;
of about 60 mM of phenol;
of about 0 mM of m-cresol;
of about 2.4 moles of zinc ions per six moles of insulin derivative;
of about 20 mM of sodium chloride; and
is having a pH value of about 7.4.

38. The pharmaceutical composition of the previous embodiments, comprising
of about 4.2 mM of insulin derivative;
of about 1.5% (weight/weight) of glycerol;
of about 60 mM of phenol;
of about 10 mM of m-cresol;
of about 2.4 moles of zinc ions per six moles of insulin derivative;
of about 20 mM of sodium chloride; and
is having a pH value of about 7.4.

39. The pharmaceutical composition of the previous embodiments, comprising of about 4.2 mM of insulin derivative; of from about 1 to about 2% (weight/weight) of glycerol; of from about 45 to about 75 mM of phenol; of from about 0 to about 15 mM of m-cresol; of from about 1.5 to about 2.5 moles of zinc ions per six moles of said insulin derivative; not more than about 50 mM of sodium chloride; and having a pH value in the range of from 7.2 to 8.0.

40. The pharmaceutical composition of the previous embodiments, comprising about 0 mM of m-cresol.

41. The pharmaceutical composition of the previous embodiments, comprising of from about 5 to about 10 mM of m-cresol.

42. The pharmaceutical composition of the previous embodiments, comprising about 10 mM of m-cresol.

43. The pharmaceutical composition according to the previous embodiments, further comprising semaglutide.

44. A pharmaceutical composition comprising A14E, B16H, B25H, B29K((N$^\varepsilon$-Eicosanedioyl-$\gamma$Glu-[2-(2-{2-[2-(2-aminoethoxy)ethoxy]acetylamino}ethoxy)ethoxy]-acetyl)), desB30 human insulin (Compound 1); and semaglutide; and further comprising of from about 1 to about 2% (weight/weight) of glycerol; of from about 45 to about 75 mM of phenol; of from 0-15 mM of m-cresol; of from about 1.5 to about 2.5 moles of zinc ions per six moles of said insulin derivative; not more than about 25 mM of sodium chloride; and having a pH value in the range of from 7.2 to 8.0

45. The pharmaceutical composition according to the previous embodiments, comprising from about 0.20 to about 0.70 mM semaglutide.

46. The pharmaceutical composition according to the previous embodiments, comprising from about 0.30 to about 0.70 mM semaglutide.

47. The pharmaceutical composition according to the previous embodiments, comprising from about 3.5 mM to about 5.0 mM A14E, B16H, B25H, B29K((N$^\varepsilon$-Eicosanedioyl-$\gamma$Glu-[2-(2-{2-[2-(2-aminoethoxy)ethoxy]acetylamino}ethoxy)ethoxy]-acetyl)), desB30 human insulin (Compound 1).

48. The pharmaceutical composition according to the previous embodiments, comprising from about 0.30 to about 0.70 mM semaglutide, and from about 3.5 mM to about 5.0 mM A14E, B16H, B25H, B29K((N$^\varepsilon$-Eicosanedioyl-$\gamma$Glu-[2-(2-{2-[2-(2-aminoethoxy)ethoxy]acetylamino}ethoxy)ethoxy]acetyl)), desB30 human insulin (Compound 1).

49. The pharmaceutical composition according to the previous embodiments, comprising about 0.30 mM semaglutide, and from about 3.5 mM to about 5.0 mM A14E, B16H, B25H, B29K((N$^\varepsilon$-Eicosanedioyl-$\gamma$Glu-[2-(2-{2-[2-(2-aminoethoxy)ethoxy]acetyl-amino}ethoxy)ethoxy]acetyl)), desB30 human insulin (Compound 1).

50. The pharmaceutical composition according to the previous embodiments, comprising about 0.40 mM semaglutide, and 4.2 mM A14E, B16H, B25H, B29K((N$^\varepsilon$-Eicosanedioyl-$\gamma$Glu-[2-(2-{2-[2-(2-aminoethoxy)ethoxy]acetylamino}ethoxy)ethoxy]-acetyl)), desB30 human insulin (Compound 1).

51. The pharmaceutical composition according to the previous embodiments, comprising about 0.49 mM or 0.50 mM semaglutide, and 4.2 mM A14E, B16H, B25H, B29K ((N$^\varepsilon$-Eicosanedioyl-$\gamma$Glu-[2-(2-{2-[2-(2-aminoethoxy)ethoxy]acetylamino}ethoxy)-ethoxy]acetyl)), desB30 human insulin (Compound 1).

52. The pharmaceutical composition according to the previous embodiments, comprising about 0.60 mM semaglutide, and 4.2 mM A14E, B16H, B25H, B29K((N$^\varepsilon$-Eicosanedioyl-$\gamma$Glu-[2-(2-{2-[2-(2-aminoethoxy)ethoxy]acetylamino}ethoxy)ethoxy]-acetyl)), desB30 human insulin (Compound 1).

53. A pharmaceutical (coformulation) composition comprising A14E, B16H, B25H, B29K((N$^\varepsilon$-Eicosanedioyl-$\gamma$Glu-[2-(2-{2-[2-(2-aminoethoxy)ethoxy]acetylamino}-ethoxy)ethoxy]acetyl)), desB30 human insulin (Compound 1); and semaglutide; and further comprising about 1.5% (weight/weight) of glycerol; of about 60 mM of phenol; about 0 mM of m-cresol; about 2.2 moles of zinc ions per six moles of said insulin derivative; about 20 mM of sodium chloride; and having a pH value of about 7.4.

54. A pharmaceutical (coformulation) composition comprising A14E, B16H, B25H, B29K((N$^\varepsilon$-Eicosanedioyl-$\gamma$Glu-[2-(2-{2-[2-(2-aminoethoxy)ethoxy]acetylamino}-ethoxy)ethoxy]acetyl)), desB30 human insulin (Compound 1); and semaglutide; and further comprising about 1.5% (weight/weight) of glycerol; of about 60 mM of phenol; about 10 mM of m-cresol; about 2.2 moles of zinc ions per six moles of said insulin derivative; about 20 mM of sodium chloride; and having a pH value of about 7.4.

55. The pharmaceutical composition of the previous embodiments, for administration to a subject in need hereof at intervals less frequent than once-daily (i.e. at intervals longer than 24 hours), during a period of time of at least 3 months, at least 6 months, or of at least 1 year.

56. The pharmaceutical composition of the previous embodiments, for administration to a subject in need for administration to the subject with a frequency in the range of from every $2^{nd}$ day to every $11^{th}$ day, on average.

57. The pharmaceutical composition of the previous embodiments, for administration to a subject in need for administration to the subject with a frequency in the range of from every 3$^{rd}$ day to every 10$^{th}$ day, on average.

58. The pharmaceutical composition of the previous embodiments, for administration to a subject in need for administration to the subject with a frequency in the range of from every 4$^{th}$ day to every day, on average.

59. The pharmaceutical composition of the previous embodiments, for administration to a subject in need for administration to the subject with a frequency in the range of from every 5$^{th}$ day to every 8$^{th}$ day, on average.

60. The pharmaceutical composition of the previous embodiments, for administration to a subject in need for administration to the subject with a frequency in the range of from every 6$^{th}$ day to every 7$^{th}$ day, on average.

61. The pharmaceutical composition of the previous embodiments, for administration to a subject in need for administration to the subject once a week, i.e. on every 7$^{th}$ day, on average, during a period of time of at least 3 months, at least 6 months, or of at least 1 year.

62. A method for making injectable pharmaceutical composition comprises:

(i) Preparing a solution by dissolving A14E, B16H, B25H, B29K((N$^ε$-Eicosanedioyl-γGlu-[2-(2-{2-[2-(2-aminoethoxy)ethoxy]acetylamino}ethoxy)ethoxy]-acetyl)), desB30 human insulin in water (ii) Preparing a solution by dissolving preservatives and isotonicity agents in water (iii) Preparing a solution by dissolving zinc ions in water (iv) Mixing solution a) and solution b)

(v) Adding solution c) to solution a+b (vi) Dissolving semaglutide in the combined solution a+b+c (vii) Adjusting the pH of mixture f) to the desired pH, followed by a sterile filtration.

Any combination of two or more of the embodiments described herein is considered within the scope of the present invention.

Biological Activity

In another aspect the invention provides pharmaceutical compositions useful as medicaments for the treatment of metabolic diseases, disorders or conditions, and, in particular, diseases, disorders or conditions relating to diabetes.

In one embodiment, the pharmaceutical composition of the invention is for use in the treatment or alleviation of a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In another embodiment, the pharmaceutical composition of the invention is for use in the treatment or alleviation of a disease, disorder or condition relating to diabetes, and in particular Type 1 diabetes, or Type 2 diabetes.

The actual dosage depends on the nature and severity of the disease being treated, and is within the discretion of the physician, and may be varied by titration of the dosage to the particular circumstances of this invention to produce the desired therapeutic effect.

BRIEF DESCRIPTION OF THE DRAWINGS

The present invention is further illustrated by reference to the accompanying drawings, in which:

FIG. 1A, FIG. 1B and FIG. 1C show oligomerisation of Compound 1 mono Formulations A, B, and C at simulated injection site conditions:

FIG. 1A: Apparent average hydrodynamic radius (rH) [nm] measured by DLS;

FIG. 1B: Apparent average molecular weight measured by CG-MALS;

FIG. 1C: Apparent average sedimentation coefficient (S) measured by AUC;

Figure 2A:
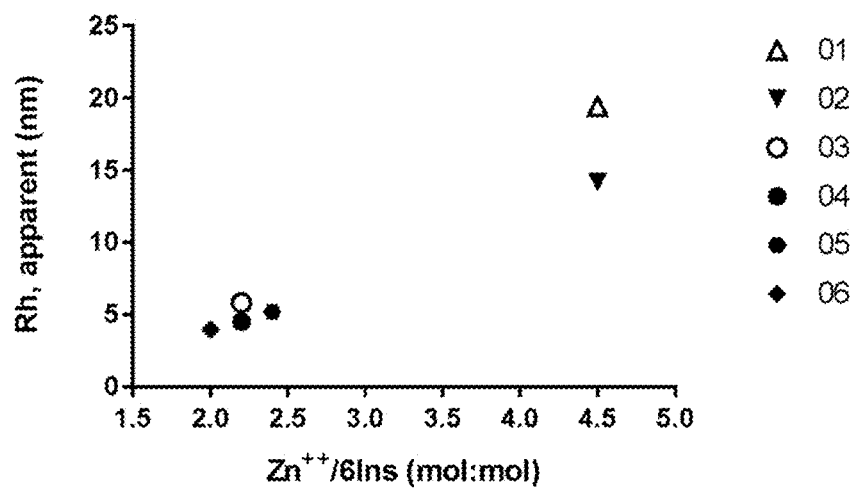
Figure 2B:
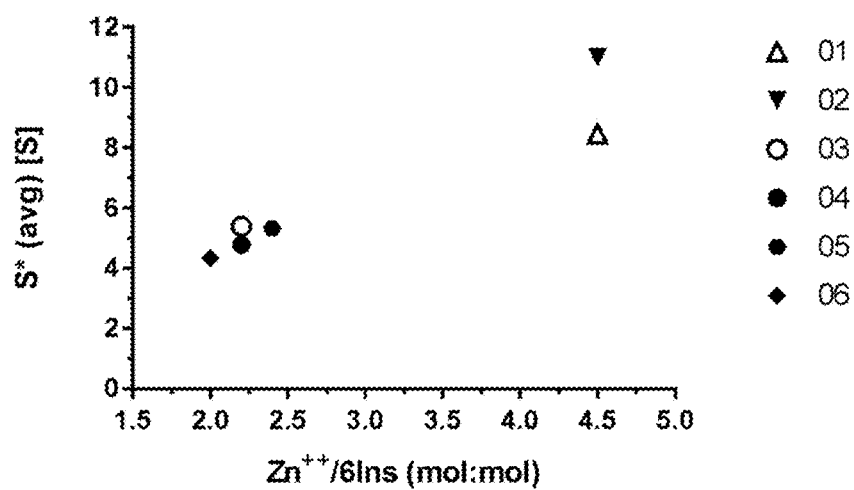

White bars: Compound 1, Formulation C with 2.2 Zn++ per six insulins (mol:mol);

Grey bars: Compound 1, Formulation B with 2.4 Zn++ per six insulins (mol:mol);

Black bars: Compound 1, Formulation A containing 4.5 Zn++ per six insulins (mol:mol);

FIG. 2A and FIG. 2B show oligomerisation of Compound 1 mono Formulations 01-06 at simulated injection site conditions:

FIG. 2A: Apparent average hydrodynamic radius (Rh, avg) [nm] measured by DLS;

FIG. 2B: Apparent average sedimentation coefficient (S*) measured by AUC

Figure 3A:
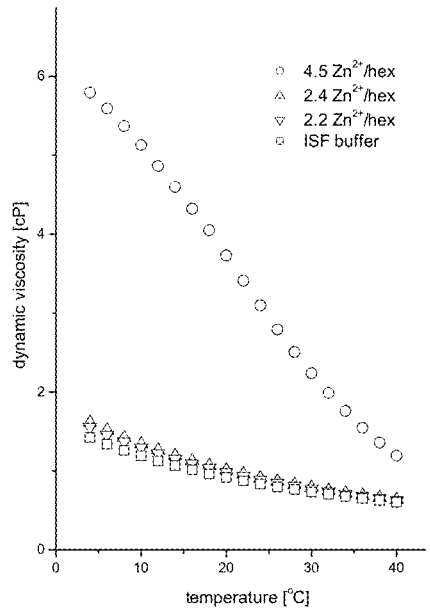
Figure 3B:
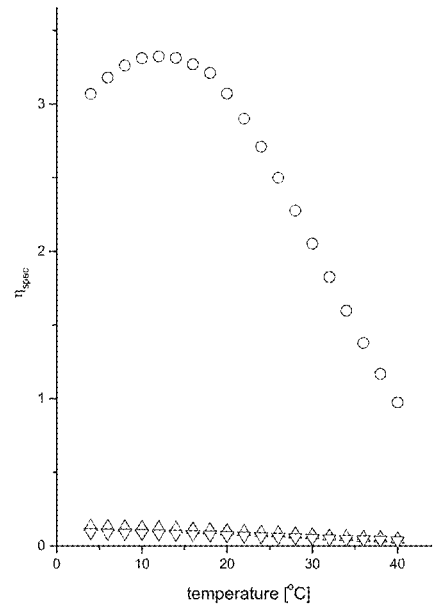
Figure 3C:
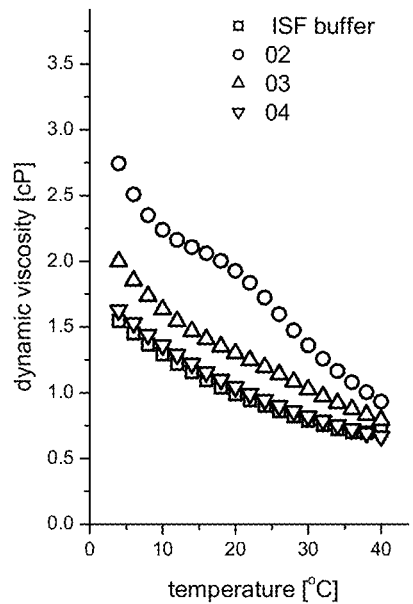
Figure 3D:
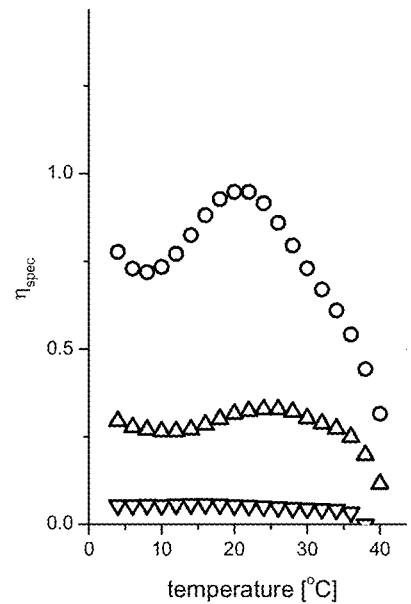
Figure 4A:
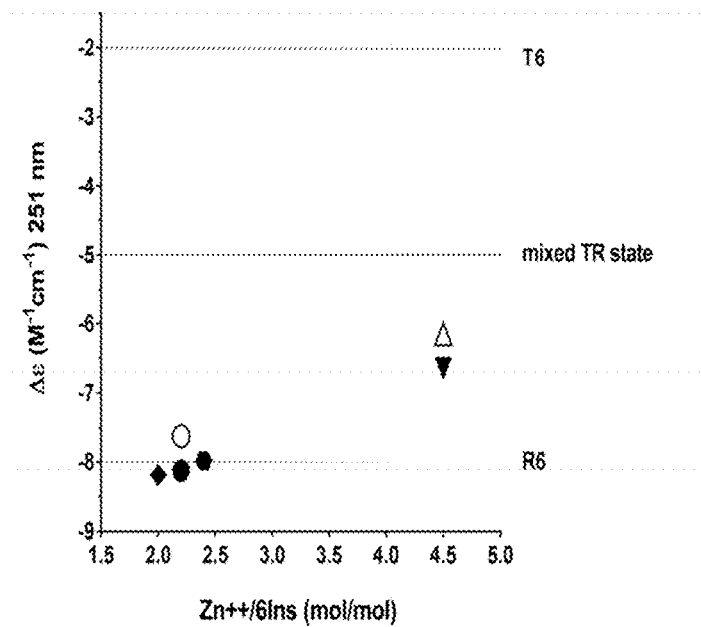
Figure 4B:
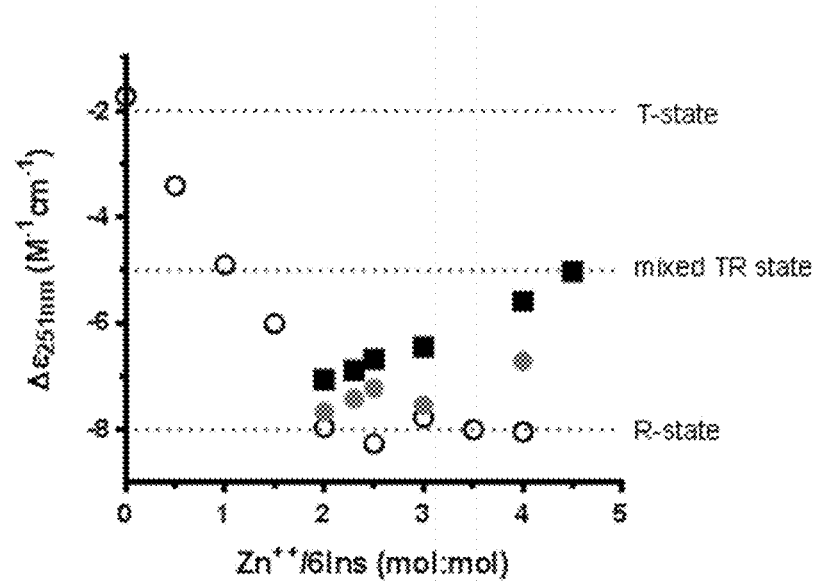
Figure 5A:
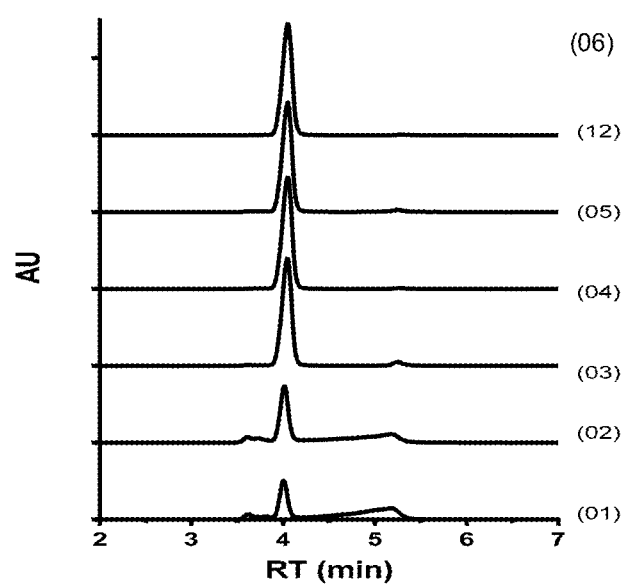
Figure 5B:
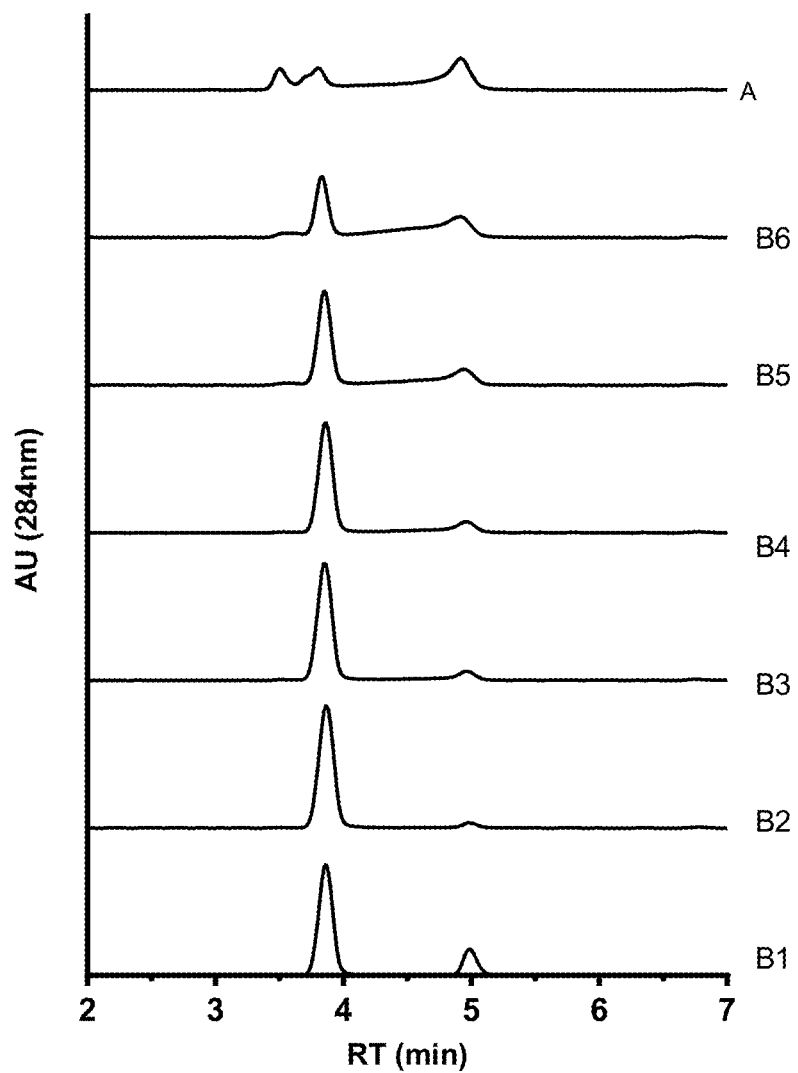
Figure 6A:
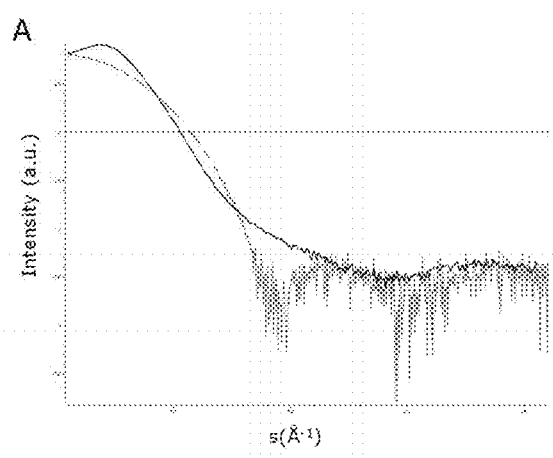
Figure 6B:
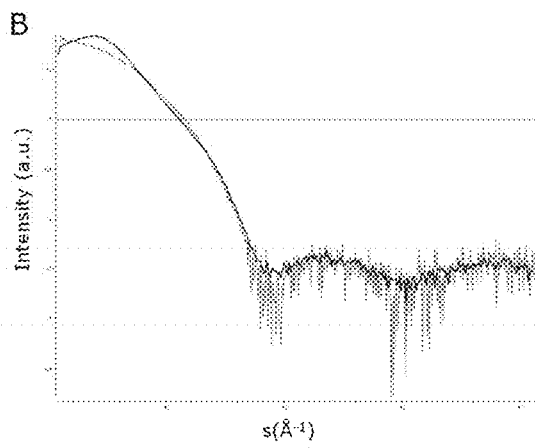
Figure 7A:
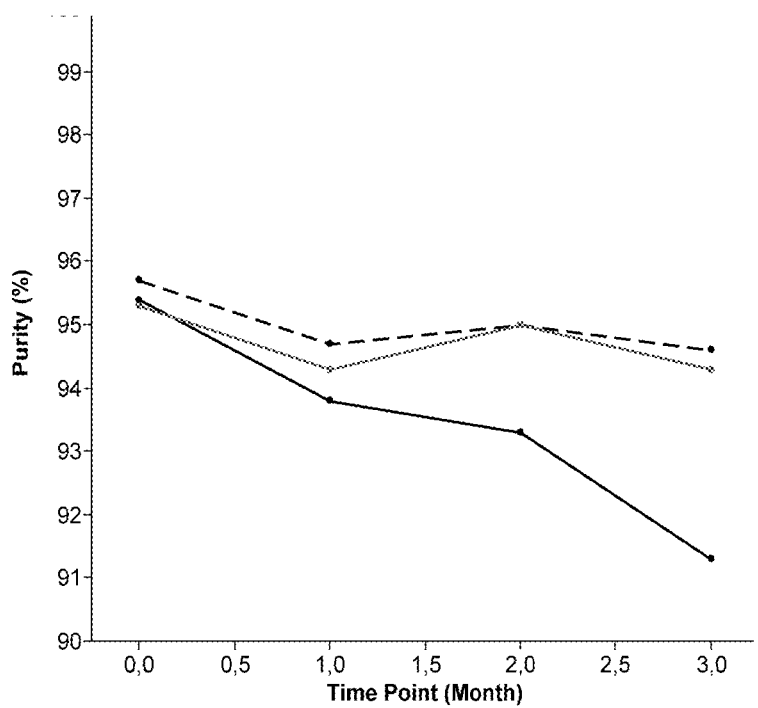
Figure 7B:
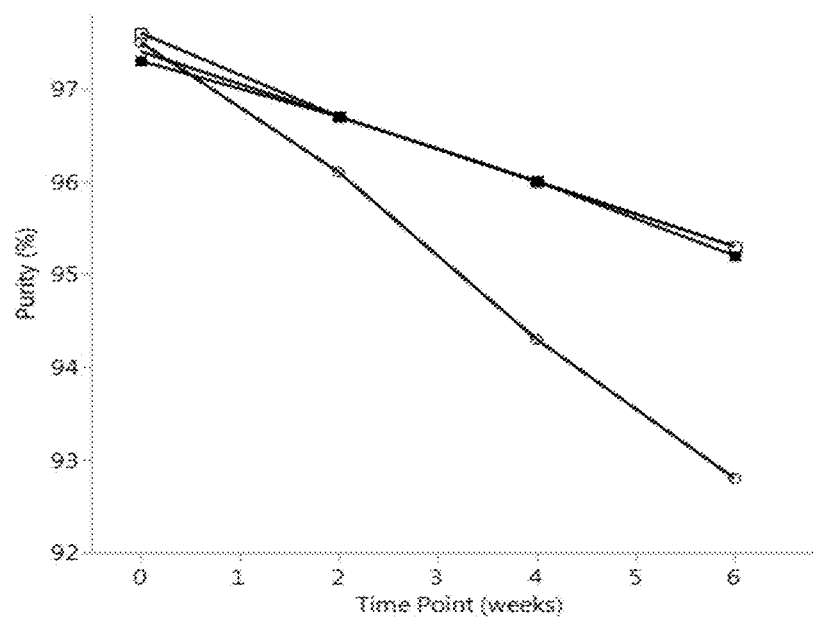
Figure 8:
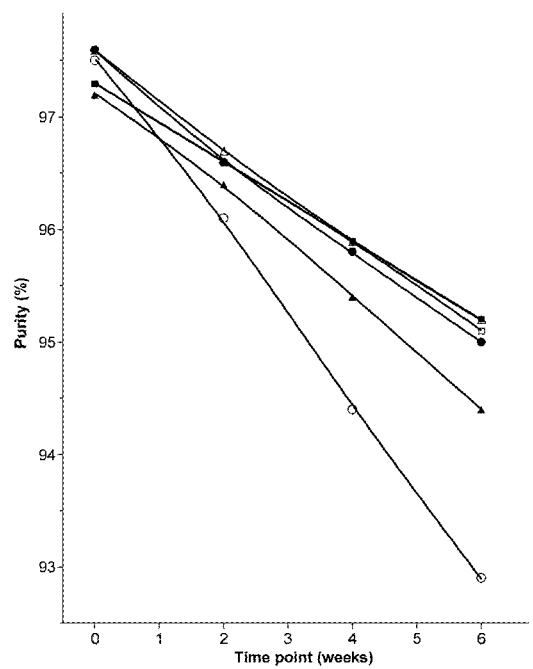
Figure 9A:
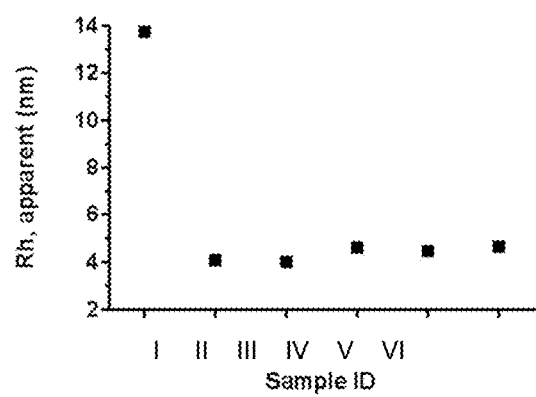
Figure 9B:
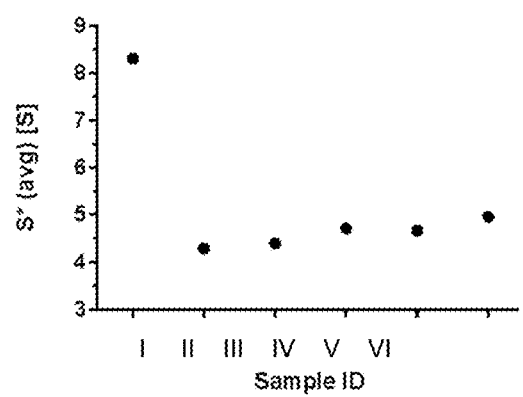

FIG. 3A-FIG. 3D show apparent dynamic viscosity [cP] (FIG. 3A, and FIG. 3C) and specific viscosity [ηspec] (FIG. 3B, FIG. 3D) of different buffer-exchanged formulations of Compound 1 and interstitial fluid buffer (ISF), as a function of temperature [° C.];

FIG. 3A and FIG. 3B: Formulation A; Formulation B; Formulation C; ISF buffer;

FIG. 3C and FIG. 3D: Formulation 02; Formulation 03; Formulation 04; ISF buffer;

FIG. 4A and FIG. 4B show conformational state of Compound 1 in formulations:

FIG. 4A: near-UV CD [Δε251 nm(M-1 cm-1)] showing conformational changes (T-state; mixed TR state; R-state) as a function of Zn++ per six insulins (mol:mol) for Formulations 01-06;

FIG. 4B: near-UV CD [Δε251 nm(M-1 cm-1)] showing conformational changes (T-state; mixed TR state; R-state) as a function of Zn++ per six insulins (mol:mol) for Formulations B1-B6, D1-D7, and human insulin formulations with various zinc level:

Open circles: Human insulin (600 nmol/ml human insulin, 30 mM phenol, 150 mM NaCl, pH 7.4);

Black squares: Compound 1 formulated with 25 mM phenol, 25 mM m-cresol and 20 mM NaCl;

Grey circles: Compound 1 formulated with 60 mM phenol, 10 mM m-cresol and 20 mM NaCl;

FIG. 5A and FIG. 5B show oligomer distribution of Compound 1 in formulations by SEC:

FIG. 5A shows native SEC chromatogram of Formulations 01, 02, 03, 04, 05, and 06;

FIG. 5B shows native SEC chromatogram of formulations A and B1-B6;

FIG. 6A and FIG. 6B show SAXS scattering data [Intensity (a.u.) vs. s(Å-1)] of Compound 1 and human insulin in the formulated state:

FIG. 6A: Scattering curves of Compound 1 Formulation A shown in black and of human insulin shown in grey (Compound 1, 4.2 mM, 4.5 Zn/hexamer; Human insulin 0.6 mM, 2.2 Zn/hexamer);

FIG. 6B: Scattering curves of Compound 1 Formulation C shown in black and of human insulin shown in grey (Compound 1, 4.2 mM, 2.2 Zn/hexamer; Human insulin 0.6 mM, 2.2 Zn/hexamer (R6-hexamer));

FIG. 7A and FIG. 7B show purity of Compound 1 in formulations:

FIG. 7A shows purity (% of total peptide) at 30° C. storage [Time Point (Month)] for Compound 1 Formulation A (black line), Formulation B (grey line) and Formulation C (dotted line);

FIG. 7B shows purity (% of total peptide) at 37° C. storage [Time Point (weeks)] for Compound 1 for Formulations 01, 04, 05 and 06;

White circles: Formulation 01, Black circles: Formulation 04, White squares: Formulation 05, Black squares: Formulation 06;

FIG. 8 shows purity of Compound 1 (% of total Compound 1) at 37° C. storage [Time Point (weeks)] in combo formulations with semaglutide:

White circles: combo-Formulation I, Black circles: combo-Formulation II, White triangles: combo-Formulation III, Black triangles: combo-Formulation IV, White squares: combo-Formulation V, Black squares: combo-Formulation VI;

FIG. 9A and FIG. 9B show oligomerisation of combo formulations at simulated injection site conditions:

FIG. 9A: Apparent average hydrodynamic radius (rH) [nm] measured by DLS;

FIG. 9B: shows the oligomer size of combo formulations after buffer exchanged as observed by AUC (S*).

EXAMPLES

The invention is further illustrated with reference to the following examples, which are not intended to be in any way limiting to the scope of the invention as claimed.

Example 1

Improved Biophysical Properties at Simulated Injection Site Conditions

Protocol

The API of the formulations is A14E, B16H, B25H, B29K((N$^\varepsilon$-Eicosanedioyl-γGlu-[2-(2-{2-[2-(2-aminoethoxy)ethoxy]acetylamino}ethoxy)ethoxy]acetyl)), desB30 human insulin (Compound 1), obtained as described in e.g. WO 2009/115469, see Example 33.

Oligomerisation of Compound 1 was determined at simulated injection site conditions. Simulated injection site conditions were achieved by depletion of phenol and/or meta-cresol, respectively, and buffer exchange into simulated interstitial fluid buffer. This procedure virtually removed all phenolic ligands but maintained the zinc/insulin ratio of the parent formulation.

Formulations are buffer-exchanged into interstitial fluid (ISF-) buffer via PD-MidiTrap G-25 column according to the manufacturers protocol.

The columns are equilibrated with the target buffer by washing the column with a sufficient volume of target buffer, and the formulation is applied in a suitable volume and eluted with target buffer. The ISF buffer consists of 140 mM NaCl, 4 mM KCl, 1 mM MgSO4, 2 mM CaCl2), 10 mM Hepes, pH 7.4.

Unless otherwise stated, the procedure was the following:
Buffer exchange at 22° C.;
Subsequent incubation at 37° C. for 14-18 hours; and
Subsequent measurement at 22° C. (except otherwise stated).

Typically measurements were conducted about 1 h after the termination of the 37° C. incubation. If this is not possible, samples are stored at 22° C. until measurement.

Unless otherwise stated, samples are measured un-diluted. It should be noted that the oligomer size resulting from the described phenol depletion procedure is process dependent, and for a given formulation it may vary with factors such as time, temperature, and batch of column. Therefore it is desirable that measurements for a given set of formulations be compared within the same experiment and not across experiments. Therefore, for the same reference formulation was tested together with various formulation of the invention in different experiments. For example, Formulation A vs. Formulation B and C; Formulation 01 vs. Formulations 02-06.

Apparent average hydrodynamic radius ($r_H$) was measured by Dynamic Light Scattering (DLS), using a DynaPro PR™ (Wyatt technology, Santa Barbara, Calif., USA). Before analysis samples were centrifuged for 5 minutes at 1200 rpm to remove any dust particles in the solution. Measurements were conducted at 25° C. using 40 acquisitions and 2 sec acquisition time.

Apparent average molecular weight (kDa) measured by Composition-Gradient, Multi-Angle Static Light Scattering (CG-MALS) using a system consisting of a Wyatt Technology Corporation (WTC) Calypso II titrator unit coupled to a WTC DAWN8+ light scattering detector (operating at 664 nm) and a WTC Optilab T-rEX refractometer (operating at 660 nm) at 25° C. The samples were filtered through a 0.45 µm filter followed by a 0.22 µm filter prior to measurement.

Sedimentation velocity (SV) experiments were performed with an XL-I Analytical Ultracentrifuge (BeckmanCoulter, Brea, Calif.) in 12-mm or 3-mm double-sector centrepieces capped with sapphire windows. Samples were spun at 40000 rpm and 20° C. until sedimentation was completed and monitored with the interference optics of the instrument. Sedimentation Coefficient Distributions (SCD) were calculated with SedFit, version 11.8 (www.analyticalultracentrifugation.com) using the c(s) model with a grid of 100 s-values over a range sufficient to describe all sedimenting material, as judged by the rmsd and the residual run pattern. The frictional ratio f/fo was treated as a variable to be optimized during fitting (P Schuck, M A Perugini, NR Gonzales, GJ Howlett and D Schubert: Size-distribution analysis of proteins by analytical ultracentrifugation: strategies and application to model systems; (Biophys. J. 2002 82:1096). Average sedimentation coefficient values were obtained via integration of the resulting c(s)-distributions.

Temperature-dependent dynamic viscosities were measured with a Lovis2000 rolling-ball type viscosimeter (Anton Paar, Graz, Austria). The temperature was decreased from 40° C. to 4° C. in 2° C. steps, allowing 5 minutes of temperature equilibration between steps. The density of the buffer was simultaneously measured with a DMA5000 densitometer, also from Anton Paar.

Three mono formulations, i.e. Formulation A representative of the prior art (see e.g. WO 2013/153000), and Formulations B, C representative of the invention (60 mM phenol/10 mM m-cresol), were prepared.

TABLE 1A

Comparative mono formulations A, B, and C

| Ingredient | Formulation A Representative of the prior art | Formulation B Representative of the invention | Formulation C Representative of the invention |
| --- | --- | --- | --- |
| Compound 1 | 4200 nmol/ml (4.2 mM) | 4200 nmol/ml (4.2 mM) | 4200 nmol/ml (4.2 mM) |
| Zinc (as zinc acetate) | 206 µg/ml (~4.5 Zn$^{++}$/hexamer) | 110 µg/ml (~2.4 Zn$^{++}$/hexamer) | 101 µg/ml (~2.2 Zn$^{++}$/hexamer) |

TABLE 1A-continued

Comparative mono formulations A, B, and C

| Ingredient | Formulation A Representative of the prior art | Formulation B Representative of the invention | Formulation C Representative of the invention |
|---|---|---|---|
| Glycerol | 16 mg/ml (1.6%) | 15 mg/ml (1.5%) | 15 mg/ml (1.5%) |
| Phenol | 2.35 mg/ml (25 mM) | 5.65 mg/ml (60 mM) | 5.65 mg/ml (60 mM) |
| Meta-cresol | 2.70 mg/ml (25 mM) | 1.08 mg/ml (10 mM) | 1.08 mg/ml (10 mM) |
| Sodium chloride | 1.17 mg/ml (20 mM) | 1.17 mg/ml (20 mM) | 1.17 mg/ml (20 mM) |
| pH | 7.4 | 7.4 | 7.4 |

Another six mono formulations, i.e. Formulation 01 (same as Formulation A), and Formulations 02, 03, 04, 05 and 06 representative of the invention, were made (Table 1B). The zinc content has been varied from 4.5 $Zn^{++}$/six insulins to 2.4, 2.2, and 2.0 $Zn^{++}$/six insulins. In addition preservative systems of either 25/25 mM phenol/m-cresol or 60/0 mM phenol/m-cresol have been tested.

TABLE 1B

Comparative formulations

| | Formulation | | | | | |
|---|---|---|---|---|---|---|
| Ingredient | 01* | 02 | 03 | 04 | 05 | 06 |
| Compound 1 (mM) | 4.2 | 4.2 | 4.2 | 4.2 | 4.2 | 4.2 |
| Zn(acetate)2 (µg/ml) | 206 | 206 | 101 | 101 | 110 | 92 |
| n Zn/6 insulin (mol/mol) | ~4.5 | ~4.5 | ~2.2 | ~2.2 | ~2.4 | ~2.0 |
| Phenol | 25 mM | 60 mM | 25 mM | 60 mM | 60 mM | 60 mM |
| m-cresol | 25 mM | 0 | 25 mM | 0 | 0 | 0 |
| glycerol | 1.6% | 1.5% | 1.6% | 1.5% | 1.5% | 1.5% |
| Vehicle (all formulations) | | | 20 mM NaCl pH 7.4 | | | |

*Same as formulation A

Improved Oligomer Size of Buffer Exchanged Mono-Formulations Having 60 mM Phenol and 10 m-Cresol (Table 2A; FIGS. 1A, 1B, and 1C)

TABLE 2A

Oligomer size at simulatied injection site

| | A | B | C |
|---|---|---|---|
| Rh(avg) [nm] | 37.31 | 9.21 | 8.37 |
| S*(avg) [S] | 17.32 | 10.53 | 9.41 |
| Mw (avg) [kDa] | 1059.8 | 190.5 | 184.7 |

Improved Oligomer Size of Buffer Exchanged Mono-Formulations Having 60 mM Phenol and 0 m-Cresol (Table 2B; FIGS. 2A and 2B)

TABLE 2B

Oligomer size at simulatied injection site

| | 01 | 02 | 03 | 04 | 05 | 06 |
|---|---|---|---|---|---|---|
| Rh(avg) [nm] | 19.42 | 14.20 | 5.83 | 4.51 | 5.20 | 3.98 |
| S*(avg) [S] | 8.46 | 11.00 | 5.39 | 4.78 | 5.33 | 4.32 |

Conclusion

The zinc content was decreased from 4.5 $Zn^{++}$/six insulins in Formulation A to 2.4 and 2.2 $Zn^{++}$/six insulins in formulations B and C (with increased phenol and decreased metacresol) respectively. This decrease in zinc was accompanied by a reduction of oligomer size (see FIGS. 1A, 1B and 1C) as determined at simulated injection site conditions by the method described above.

Results from formulation 01-06 further confirm that the oligomer size is reduced when Zn is reduced from 4.5 $Zn^{++}$/six insulins to 2.2±0.2 $Zn^{++}$/six insulins. For 2.2±0.2 $Zn^{++}$/six insulins the oligomer size is further reduced when phenol/cresol is reduced from 25 mM/25 mM to 60 mM/0 mM. See FIGS. 2A and 2B.

Improved Viscosity of Buffer Exchanged Mono-Formulations Having 60 mM Phenol and 10 mM m-Cresol (See Table 3A; FIGS. 3A and 3B)

TABLE 3A

Viscosity of buffer-exchanged Formulations A, B, C

| | Dynamic viscosity (cP) Formulation | | | | Specific viscosity Formulation | | |
|---|---|---|---|---|---|---|---|
| temp (C.) | A | B | C | ISF buffer | A | B | C |
| 40 | 1.194 | 0.633 | 0.628 | 0.605 | 0.97355 | 0.04628 | 0.03802 |
| 38 | 1.359 | 0.659 | 0.653 | 0.627 | 1.16746 | 0.05104 | 0.04147 |
| 36 | 1.548 | 0.687 | 0.68 | 0.651 | 1.37788 | 0.0553 | 0.04455 |
| 34 | 1.758 | 0.718 | 0.709 | 0.677 | 1.59675 | 0.06056 | 0.04727 |
| 32 | 1.989 | 0.751 | 0.74 | 0.704 | 1.82528 | 0.06676 | 0.05114 |
| 30 | 2.237 | 0.787 | 0.773 | 0.733 | 2.05184 | 0.07367 | 0.05457 |
| 28 | 2.506 | 0.825 | 0.809 | 0.765 | 2.27582 | 0.07843 | 0.05752 |
| 26 | 2.792 | 0.866 | 0.847 | 0.798 | 2.49875 | 0.08521 | 0.0614 |
| 24 | 3.098 | 0.91 | 0.889 | 0.835 | 2.71018 | 0.08982 | 0.06467 |
| 22 | 3.409 | 0.958 | 0.934 | 0.874 | 2.90046 | 0.09611 | 0.06865 |
| 20 | 3.729 | 1.01 | 0.982 | 0.916 | 3.07096 | 0.10262 | 0.07205 |
| 18 | 4.051 | 1.066 | 1.035 | 0.962 | 3.21102 | 0.10811 | 0.07588 |
| 16 | 4.321 | 1.126 | 1.092 | 1.012 | 3.26976 | 0.11265 | 0.07905 |
| 14 | 4.597 | 1.191 | 1.153 | 1.066 | 3.31238 | 0.11726 | 0.08161 |
| 12 | 4.865 | 1.262 | 1.22 | 1.125 | 3.32444 | 0.12178 | 0.08444 |
| 10 | 5.131 | 1.338 | 1.293 | 1.19 | 3.31176 | 0.12437 | 0.08655 |
| 8 | 5.369 | 1.421 | 1.372 | 1.26 | 3.26111 | 0.12778 | 0.08889 |
| 6 | 5.593 | 1.514 | 1.458 | 1.338 | 3.18012 | 0.13154 | 0.08969 |
| 4 | 5.795 | 1.612 | 1.556 | 1.424 | 3.06952 | 0.13202 | 0.0927 |

Improved Viscosity of Buffer Exchanged Mono-Formulations Having 60 mM Phenol and 0 m-Cresol (See Table 3B; FIGS. 3C and 3D)

TABLE 3B

Viscosity of buffer exchanged Formulations 02, 03 and 04

| | Dynamic viscosity (cP) Formulation | | | | Specific viscosity Formulation | | |
|---|---|---|---|---|---|---|---|
| | ISF | 02 | 03 | 04 | 02 | 03 | 04 |
| 3.99 | 1.5447 | 2.7441 | 1.9996 | 1.6278 | 0.77646 | 0.29449 | 0.0538 |
| 6 | 1.4513 | 2.5087 | 1.8529 | 1.5296 | 0.72859 | 0.27672 | 0.05395 |

TABLE 3B-continued

Viscosity of buffer exchanged Formulations 02, 03 and 04

| | Dynamic viscosity (cP) Formulation | | | | Specific viscosity Formulation | | |
|---|---|---|---|---|---|---|---|
| | ISF | _02 | _03 | _04 | _02 | _03 | _04 |
| 8 | 1.3668 | 2.3492 | 1.7355 | 1.4414 | 0.71876 | 0.26975 | 0.05458 |
| 10 | 1.2917 | 2.2389 | 1.6335 | 1.3615 | 0.7333 | 0.26461 | 0.05404 |
| 12 | 1.2209 | 2.1624 | 1.5448 | 1.2894 | 0.77115 | 0.2653 | 0.05611 |
| 14 | 1.1555 | 2.1078 | 1.4678 | 1.2215 | 0.82415 | 0.27027 | 0.05712 |
| 16 | 1.095 | 2.06 | 1.4063 | 1.1575 | 0.88128 | 0.28429 | 0.05708 |
| 18 | 1.04 | 2.0041 | 1.3516 | 1.0984 | 0.92702 | 0.29962 | 0.05615 |
| 20 | 0.9893 | 1.927 | 1.3014 | 1.043 | 0.94784 | 0.31548 | 0.05428 |
| 22 | 0.9423 | 1.8351 | 1.247 | 0.9916 | 0.94747 | 0.32336 | 0.05232 |
| 24 | 0.8991 | 1.7221 | 1.1941 | 0.9447 | 0.91536 | 0.32811 | 0.05072 |
| 26 | 0.8588 | 1.597 | 1.1404 | 0.9003 | 0.85957 | 0.3279 | 0.04832 |
| 28 | 0.8216 | 1.4748 | 1.085 | 0.8594 | 0.79503 | 0.32059 | 0.04601 |
| 30 | 0.7869 | 1.3608 | 1.0249 | 0.8219 | 0.72932 | 0.30245 | 0.04448 |
| 32 | 0.7544 | 1.2594 | 0.9713 | 0.7867 | 0.66941 | 0.28751 | 0.04282 |
| 34 | 0.7239 | 1.1654 | 0.9215 | 0.754 | 0.60989 | 0.27297 | 0.04158 |
| 36 | 0.7004 | 1.0795 | 0.8749 | 0.7236 | 0.54126 | 0.24914 | 0.03312 |
| 38 | 0.6951 | 1.0027 | 0.8321 | 0.6948 | 0.44253 | 0.19709 | −4.32E−04 |
| 40 | 0.7107 | 0.9345 | 0.7927 | 0.6682 | 0.3149 | 0.11538 | −0.0598 |

Conclusion

These experiments show that the viscosity of the formulation at simulated injection site conditions according to this method are highly dependent on the zinc content such that decreasing the zinc ratio leads to lower viscosity.

Example 2

$t_{max}$ and Elimination $t_{1/2}$ $t_{max}$ represents the time to maximum concentration (maximal plasma exposure), and $t_{1/2}$ represents the elimination half-life in which half of the compound disappears from plasma following administration.

The altered biophysical properties described in Example 1 are consistent with a PK profile exhibiting earlier $t_{max}$ in pigs (see Table 3). This indicates that the residence time of Compound 1 in the sub-cutis is reduced when formulated according to the invention, and in contrast to the same compound being provided in a formulation according to the prior art.

Surprisingly, the reduced zinc level almost has no impact on the duration of action (i.e. elimination $t_{1/2}$ is not affected), which makes the formulation according to the invention and the formulation of the prior art equally suited for once-weekly administration.

TABLE 4

| Formulation | Species | $t_{max}$ (hours) | $t_{1/2}$ (hours) |
|---|---|---|---|
| Compound 1, Formulation A 4.5 zinc/hexamer, 25 mM phenol, 25 mM m-cresol | Pig Human | 20 42 | 47 185 |
| Compound 1, Formulation C 2.2 zinc/hexamer, 60 mM phenol, 10 mM m-cresol, 20 mM NaCl | Pig | 8 | 45 |

Conclusion

These experiments show that the residence time in the sub-cutis ($t_{max}$) of Compound 1 was significantly reduced as a result of reducing $Zn^{++}$/hexamer. The observation is consistent with data presented in Example 1, which show a reduction of the size of the oligomers formed at simulated injection site conditions.

Thus, when formulated according to the invention, Compound 1 forms smaller oligomers at the site of injection resulting in a PK/PD profile with a shorter residence time in the sub-cutis (decreased $t_{max}$).

But surprisingly, although the residence time in the sub-cutis ($t_{max}$) of Compound 1 was significantly reduced, the formations of the invention maintained the same elimination half-life (elimination $t_{1/2}$ is not affected). This means the formulations of the invention could facilitate the long-acting insulin derivatives to more quickly reach to the maximum concentration in circulation, while still maintain the maximum concentration with longer duration.

This unexpected finding also makes it possible to limit the formation of large oligomers at the site of injection, while still preserving a long duration of action commensurate with a once-weekly administration profile. Formation of large oligomers with high viscosity at the site of injection may introduce discomfort upon injection.

Example 3

Improved Conformational State in Formulation

With presence of zinc, human insulin exists as hexamers in formulation. Human insulin hexamers can adopt two different conformational states depending on the conformation of the monomers. The eight N-terminal amino acid residues of the insulin monomer B-chain can be in either an extended conformation (T-state) or an α-helical conformation (R-state). In the presence of phenol and NaCl, human insulin adopts the R conformation, which is the favourable conformation with regards to physical and chemical stability (Dunn M F. Zinc-ligand interactions modulate assembly and stability of the insulin hexamer: A review. Biometals 2005; 18; 295-303).

Protocol

The conformational changes of the insulin hexamer were followed by the 251 nm CD-signature (Krüger P, Gilge G, Cabuk Y and Wollmer A; *Biol. Chem. Hoppe-Seyler* 1990 371 669-673). Samples were measured using a Jasco 815 instrument and a pathlenght of 0.02 cm. Blank titrations were subtracted and the resulting Δε 251 nm was plotted vs Zn/6Ins (mol/mol).

Conformational State of Mono-Formulations Having 60 mM Phenol/0 m-Cresol

The conformational state of Formulations 01-06 is shown in Table 5A and FIG. 4A.

TABLE 5A

Conformational state propensity in formulation 01-06 with 60 mM phenol/0 m-cresol

| Formulation | 01 | 02 | 03 | 04 | 05 | 06 |
|---|---|---|---|---|---|---|
| R-state propensity $\Delta\varepsilon$ (M−1 cm−1) @251 nm | −6.15 | −6.65 | −7.63 | −8.12 | −7.98 | −8.19 |

FIG. 4A shows the conformational changes (T-state; mixed TR state; R-state) as a function of $Zn^{++}$ per six insulins (mol:mol) for formulations 01-06.

Conformational State of Mono-Formulations Having 60 mM Phenol and 10 mM m-Cresol Two series of formulations were prepared. All formulations comprised 4.2 mM of Compound 1, 16 mg/ml (1.6%) glycerol, 20 mM NaCl, with pH of 7.4. Series B formulations comprised 60 mM phenol and 10 mM m-cresol, with zinc level varied as 1.5 (B1), 2.0(B2), 2.3(B3), 2.5(B4), 3.0(B5), and 4.0(B6) per 6 insulin. Series D comprised 25 mM phenol and 25 mM m-cresol, with zinc level varied as 1.5, 2.0, 2.3, 2.5, 3.0, 4.0 and 4.5 per 6 insulin. Also a series of human insulin formulations were prepared, with various zinc level. The conformational state is shown in Table 5B and FIG. 4B.

TABLE 5B

Conformational state propensity in formulations B1-B6 with 60 mM phenol and 10 m-cresol, and formulations D1-D7 with 25 mM phenol and 25 m-cresol

| | R-state propensity $\Delta\varepsilon$ (M−1cm−1) @251 nm | |
|---|---|---|
| Zn/6Ins | Series B 60/10 phe/cre | Series D 25/25 phe/cre |
| *1.5 | −6.83 (B1) | −6.58 (D1) |
| 2.0 | −7.67 (B2) | −7.06 (D2) |
| 2.3 | −7.42 (B3) | −6.88 (D3) |
| 2.5 | −7.23 (B4) | −6.67 (D4) |
| 3.0 | −7.54 (B5) | −6.45 (D5) |
| 4.0 | −6.72 (B6) | −5.58 (D6) |
| 4.5 | n.a. | −5.03 (D7) |

*Not included in FIG. 4B

FIG. 4B shows conformational changes (T-state; mixed TR state; R-state) as a function of Zn++ per six insulins (mol:mol) for Series B and Series D formulations, and human insulin formulations.

Conclusion

Near-UV CD data show that the T/R conformation of Compound 1 was dependent on the zinc concentration. A decrease in zinc was accompanied by a change in conformational state of Compound 1 in the formulation from a mixed T/R state to the R-state, which was also accompanied by a higher level of hexamer formed in the formulations (see Example 4 below). The R-state and hexmer level was further enhanced by a change in phenol/meta-cresol ratio from 25/25 mM to 60/10 mM (FIG. 4B).

The data of formulations 01-06 show that R-state of Compound 1 in the formulations is are further enriched by decreasing Zn from 4.5 to 2.2Zn±0.2Zn/6 Compound 1 and by omitting m-cresol (FIG. 4A).

Example 4

Improved Oligomer Distribution in Formulation

Protocol

Size Exclusion Chromatography is a sensitive method for quantifying the non-covalent oligomer distribution of insulin formulations. SEC was conducted using a BEH200 column, 1.7 μm 4.6×150 mm with a running buffer consisting of 8.0 mM phenol, 140 mM NaCl, 10 mM Tris-HCl, pH 7.4. Chromatography was conducted at 22 C using 2 μL injection volume and a flow of 0.3 ml/min. As molecular weight standards albumin, a covalent insulin hexamer, and a monomeric insulin were used. Chromatograms were analysed by integration to represent species larger than hexamer (3.0-3.8 min), hexamer (3.8-4.3 min), and species smaller than hexamer (4.3-5.5 min). Please note that exact integration limits for each data set will vary slightly due to variations in column performance.

Small angle X-ray scattering (SAXS) data were collected using a BioSAXS-2000 instrument equipped with a flow cell and a Dectris 100K detector covering a q-range of 0.008-0.661 Å$^{-1}$. Buffer measurements were subtracted from sample measurements to get the protein scattering profiles. Data from a reference sample of human insulin in a hexameric state with R conformation was collected according to the same procedure, from a sample of 0.6 mM human insulin, 3 $Zn^{++}$/six insulins, 16 mM phenol, 20 mM NaCl and 7 mM phosphate buffer pH 7.4.

Oligomer Distribution for Formulations Comprising 60 mM Phenol and 0 m-Cresol

Native SEC chromatogram comparing formulations 01, 02, 03, 04, 05, and 06 has been generated (see Table 6 and FIG. 5A).

TABLE 6

Species distribution as obtained by native SEC by integration of chromatograms

| | | Formulation | | | | | |
|---|---|---|---|---|---|---|---|
| Peak assignment | | 01 | 02 | 03 | 04 | 05 | 06 |
| | | % species in formulation | | | | | |
| (3.0-3.8 min) | Larger than hexamer | 8.8 | 9.4 | 1.1 | 0.6 | 0.7 | 0.2 |
| (3.8-4.3 min) | Hexamer | 34.5 | 48.9 | 95.1 | 98.1 | 95.9 | 98.9 |
| (4.3-5.5 min) | smaller than hexamer | 56.8 | 41.7 | 3.8 | 1.3 | 3.5 | 0.9 |

Oligomer Distribution for Formulations Comprising 60 mM Phenol and 10 mM m-Cresol Native SEC chromatogram comparing formulations B1-B6 and formulation A has been generated (see Table 6 and FIG. 5B). The area under the curve is similar for all chromatograms. Chromatograms were analysed by integration to represent species larger than hexamer (3.0-3.8 min), hexamer (3.8-4.3 min), and species smaller than hexamer (4.3-5.5 min). Please note that exact integration limits for each data set will vary slightly due to variations in column performance.

TABLE 7

Oligomer distribution by SEC

| Peak assignment | B1 | B2 | B3 | B4 | B5 | B6 | A |
|---|---|---|---|---|---|---|---|
| | \% species in formulation | | | | | | |
| Larger than hexamer | 0.2 | 0.5 | 0.8 | 0.7 | 2.2 | 4.9 | 18.2 |
| Hexamer | 80.3 | 94.8 | 86.7 | 82.1 | 65.5 | 41.8 | 22.0 |
| smaller than hexamer | 19.5 | 4.8 | 12.5 | 17.2 | 32.3 | 53.3 | 59.8 |

Conclusion

SEC data of Formulations 01-06 (Table 6, FIG. 5A) show that the oligomer distribution of Compound 1 Formulation 01 is characterised by broad bands with no clear dominant oligomer species. The oligomer distribution of Compound 1 in Formulations 03-06 is narrower compared to Formulations 01 and 02. The retention time of the main peak Formulations 03-06 is consistent with a hexamer and the small peak with a retention time of 5 minutes is consistent with a monomer or dimer.

SEC data of Formulations B1-B6 and A (Table 7, FIG. 5B) also show that with 2.0-2.5 zinc/6 insulins, the hexamer peak is enriched to 4.0 or 4.5 Zn.

Therefore, the hexamer peak is enriched at low zinc (e.g., 2.0Zn to 2.5Zn) compared to high zinc (e.g. 4.0 or 4.5Zn). For both 4.5Zn and 2.2Zn the hexamer is enriched at 60 mM/0 or 10 mM phenol/m-cresol relative to 25/25 mM phenol/m-cresol. When formulated according to the invention the hexamer content is increased and the oligomerisation becomes more well-defined.

SAXS data also confirm that the oligomerisation pattern of Compound 1 Formulation A with 4.5 $Zn^{++}$/hexamer does not resemble the classical human insulin hexamer while a hexamer-based structure of the Compound 1 is dominant in Formulation C (FIG. 6). When formulated according to the invention (Formulation C) the oligomerisation pattern becomes more well-defined and consistent with a hexamer based structure similar to human insulin.

Example 5

Improved Chemical Stability and Physical Stability

Experimental results in this example showed that both chemical stability and physical stability of Compound 1 are improved of the new formulations compared with the reference Formulation A. In particular, with high level of phenol and low level of m-cresol, both chemical stability and physical stability of Compound 1 increases when zinc concentration decreases.

Protocol

Purity was determined by reversed phase ultra-high performance liquid chromatography (RP-UHPLC) where the samples were analysed using a Acquity CSH Fluoro Phenyl, 130 Å, 1.7 μm, 2.1×150 mm column, gradient elution by acetonitrile in a mobile phase of acetonitrile and phosphoric buffer in water with subsequent UV detection (215 nm) under a flow of 0.30 ml/min with a sample injection volume of 2-3 μl. Purity was evaluated as the area of the main peak divided by the area of all peaks×100%.

Chemical Stability of Compound 1 Formulation with 60 mM Phenol and 10 mM m-cresol The stability measured as % purity of total peptide with RP-UHPLC shows an significantly increased stability of Compound 1 in Formulation B and Formulation C, which comprised 60 mM phenol and 10 mM m-cresol, compared to Compound 1 Formulation A, which comprised 25 mM phenol and 25 mM m-cresol. See Table 8 and FIG. 7A.

TABLE 8

% Purity of Compound 1

| | Storage time at 30° C. (Months) | | | |
|---|---|---|---|---|
| Formulation | 0 | 1 | 2 | 3 |
| A | 95.4 | 93.8 | 93.3 | 91.3 |
| B | 95.3 | 94.3 | 95.0 | 94.3 |
| C | 95.7 | 94.7 | 95.0 | 94.6 |

Chemical Stability of Compound 1 Formulations with 60 mM Phenol and 0 m-Cresol

The stability of formulations presented in table 9 measured as % purity of total peptide with RP-UHPLC further confirms that the chemical stability of Compound 1 increases as a function of zinc concentration in formulations with relatively high level of phenol and low level of m-cresol. The results show an increased stability of Compound 1 when zinc was decreased from 4.5 $Zn^{++}$/six insulins to 2.4, 2.2 and 2.0 $Zn^{++}$/six insulins in formulations with a change in preservative system from 25/25 mM phenol/m-cresol to 60 mM phenol and 0 m-cresol. See Table 9 and FIG. 7B.

TABLE 9

% Purity of Compound 1

| | Storage time at 37° C. (weeks) | | | |
|---|---|---|---|---|
| Formulation | 0 | 2 | 4 | 6 |
| 01 | 97.5 | 96.1 | 94.3 | 92.8 |
| 04 | 97.4 | 96.7 | 96.0 | 95.3 |
| 05 | 97.6 | 96.7 | 96.0 | 95.3 |
| 06 | 97.3 | 96.7 | 96.0 | 95.2 |

Conclusion

When formulated according to the invention (see Formulations B, C, 04, 05, and 06; Tables 8 and 9, and FIG. 7A and FIG. 7B) the chemical stability increases compared to prior art (Formulations A and Formulation 01).

Physical Stability

Protocol:

The Compound 1 formulations were tested in a 96-well microtiter plate with 4 replica of 200 μl. To 1.0 ml from each formulation, ThT (thioflavin T) was added to 1 μM. Thioflavin T (ThT) assay for propensity to form amyloid fibrils was performed on Thermo Fluoroskan, 960 rpm shaking, 37° C., for 45 hours. ThT emission was scanned before and after assay. The lag time until on-set of ThT fluorescence emission is a measurement of physical stability. Lag times were determined from fluorescence curves averaged over 4 replica. A longer lag-time is indicative of higher physical stability.

It should be noted that the ThT results obtained from the described protocol may vary between experiments. Therefore it is desirable that measurements for a given set of formulations be compared within the same experiment and not across experiments. In this Example, the same reference formulation was tested together with various formulations of the invention in different experiments. For example, Formulation A vs. Formulation C; Formulation 01 vs. Formulations 04-06.

The lag times are shown in Table 10 below. Formulation A or Formulation 01 as reference formulation for comparison.

The results are show in Table 10A and Table 10B.
Physical Stability of Compound 1 in Formulations with 60 mM Phenol and 10 m-Cresol

TABLE 10A

Tht lag times (1)

|  | Formulation C | Formulation A |
|---|---|---|
| Lag time (hrs) | 11.3 | 10.0 |

TABLE 10B

Tht lag times (2)

|  | 01 | 04 | 05 | 06 |
|---|---|---|---|---|
| Lag time (hrs) | 9.7 | 29.3 | 13.3 | >45 |

Conclusion

The lag-times obtained in the ThT assay indicates that the physical stability of Compound 1 is improved in formulations with low level of zinc, high level of phenol, and low level of m-cresol. The data showed that when decreasing zinc from 4.5Zn/6Ins to 2.2±0.2Zn/6Ins and concomitant increasing phenol from 25 mM to 60 mM and decreasing m-cresol from 25 mM to 10 mM lead to longer lag time and thus improved physical stability. With m-cresol being removed, the physical stability of Compound 1 was further improved in formulations with low zinc level (see Table 10B).

Example 6

Combo-Formulations and the Chemical and Physical Stability Thereof

Compound 1 may be co-formulated together with the once-weekly GLP-1 analogue semaglutide for a fixed-ratio combination.

The following combo-formulations 1 to 6 of Compound 1 and semaglutide were prepared. The mono-formulation of Compound 1 was also prepared as mono-formulation reference 1. The intended target values are shown in Table 11, below.

The concentrations of Compound 1 and semaglutide in the produced formulations were measured using RP-HPLC and reference materials. These concentrations are stated in Table 12A and 12B, below.

TABLE 12A

Measured concentrations of Compound 1 and semaglutide

|  | Mono Reference-1 | Combo 1 | Combo 2 | Combo 3 | Combo 4 |
|---|---|---|---|---|---|
| Compound 1 (mM) Measured | 4.1 | 4.1 | 4.1 | 4.1 | 4.1 |
| Semaglutide (mM) Measured | n.a. | 0.5 | 0.4 | 0.6 | 0.3 |

TABLE 12B

Measured concentrations of Compound 1 and semaglutide (a separate batch from Table 12A)

|  | Mono reference-1 | Combo 5 | Combo 6 |
|---|---|---|---|
| Compound 1 (mM) Measured | 4.2 | 4.3 | 4.3 |
| Semaglutide (mM) Measured | n.a. | 0.49 | 0.49 |

The measured concentrations thus deviated less than 3% from the intended target values.

The following combo-formulations I-VI of Compound 1 and semaglutide were also prepared later. The mono-formulation of Compound 1 was prepared as mono-formulation reference 2. The intended target values are shown in Table 13, below.

TABLE 11

Combo-formulations of Compound 1 and semaglutide

|  | Mono Reference 1 | Combo 1 | Combo 2 | Combo 3 | Combo 4 | Combo 5 | Combo 6 |
|---|---|---|---|---|---|---|---|
| Compound 1 (mM) | 4.2 | 4.2 | 4.2 | 4.2 | 4.2 | 4.2 | 4.2 |
| Semaglutide (mM)/(mg/ml) | n.a. | 0.49/2.0 | 0.4/1.6 | 0.6/2.4 | 0.3/1.25 | 0.49/2.0 | 0.49/2.0 |
| $Zn(acetate)_2$ (mM) | 1.54 | 1.54 | 1.54 | 1.54 | 1.54 | 1.4 | 1.75 |
| n Zn/6 insulin | ~2.2 | ~2.2 | ~2.2 | ~2.2 | ~2.2 | ~2.0 | ~2.5 |
| Vehicle (all formulations) | | | | 60 mM phenol 10 mM m-cresol 1.5% glycerol 20 mM NaCl pH 7.4 | | | |

TABLE 13

|  | Mono Reference 2 | Combo I | Combo II | Combo III | Combo IV | Combo V | Combo VI |
|---|---|---|---|---|---|---|---|
| Compound 1 (mM) | 4.2 | 4.2 | 4.2 | 4.2 | 4.2 | 4.2 | 4.2 |
| Semaglutide (mM)/(mg/ml) | n.a. | 0.49/2.0 | 0.49/2.0 | 0.3/1.25 | 0.49/2.0 | 0.49/2.0 | 0.3/1.25 |
| Zn(acetate)$_2$ (µg/ml) | 101 | 206 | 101 | 101 | 101 | 110 | 110 |
| n Zn/6 insulin | ~2.2 | ~4.5 | ~2.2 | ~2.2 | ~2.2 | ~2.4 | ~2.4 |
| Phenol | 60 mM | 25 mM | 60 mM | 60 mM | 25 mM | 60 mM | 60 mM |
| m-cresol | 0 | 25 mM | 0 | 0 | 25 mM | 0 | 0 |
| Vehicle (all formulations) |  |  |  | 1.5% glycerol 20 mM NaCl pH 7.4 |  |  |  |

Physical Stability

Protocol: The formulations were tested in a 96-well microtiter plate with 8 replica of 200 µl. To 1.0 ml from each formulation, ThT (thioflavin T) was added to 1 µM. Thioflavin T (ThT) assay for propensity to form amyloid fibrils was performed on Thermo Fluoroskan, 960 rpm shaking, 37° C., for 45 hours. ThT emission was scanned before and after assay. The lag time until on-set of ThT fluorescence emission (formation of amyloid fibrils) is a measurement of physical stability. Lag times were determined from fluorescence curves averaged over 8 replica. Lag times were tested twice for combo formulations 1-4 and combo formulations 5 and 6, respectively; and each with mono formulation tested as a reference, to make the results comparable. A longer lag-time is indicative of higher physical stability.

The Compound 1 mono-formulation reference and the combo-formulations were tested in a 96-well microtiter plate Thioflavin T (ThT) assay for propensity to form amyloid fibrils.

The lag times are shown in Table 14A, 14B, 14C below.

TABLE 14A

Combo-formulation lag times

|  | Mono Reference 1 | Combo 1 | Combo 2 | Combo 3 | Combo 4 |
|---|---|---|---|---|---|
| Lag time (hrs) | 11.0 | 19.3 | 18.0 | 21.6 | 23 |

TABLE 14B

Combo-formulation lag times

|  | Mono Reference 1 | Combo 5 | Combo 6 |
|---|---|---|---|
| Lag time (hrs) | 9.9 | 20.6 | 45 |

TABLE 14C

Combo-formulation lag times

|  | Mono reference 2 | Combo I | Combo II | Combo III | Combo IV | Combo V | Combo VI |
|---|---|---|---|---|---|---|---|
| Lag time (hrs) | 29.3 | 44.3 | 45 | 45 | 28.6 | 45 | 45 |

Conclusion:

The ThT assay indicated that without increasing zinc level, combo formulations of Compound 1 and semaglutide did not compromise the physical stability of Compound 1 compared to that of the Compound 1 mono-formulation. In fact, the lag times of the combo-formulations were much longer than that of the Compound 1 mono-formulation, showing the co-formulating of Compound 1 with semaglutide in fact stabilizes the formulation towards the unwanted amyloid fibril formation. Compared with combo-formulation of other long acting insulin derivative and GLP-1 derivative (e.g. degludec and liraglutide), this finding is unexpected and surprising.

Table 14C results show that lowering the level of m-cresol can further improve the physical stability of the combo-formulation of Compound 1 and semaglutide; and increasing the level of phenol also improves the physical stability of the combo-formulation of Compound 1 and semaglutide.

Table 14C results also show that when co-formulating Compound 1 with semaglutide in a formulation according to the invention, the physical stability of Compound 1 increases, compared to using prior art formulation (Formulation I) for combo-formulation of Compound 1 and semaglutide.

Chemical Stability

Protocol

Purity was determined by reversed phase ultra-high performance liquid chromatography (RP-UHPLC) where the samples were analysed using a Acquity CSH Fluoro Phenyl, 130 Å, 1.7 um, 2.1×150 mm column, gradient elution by acetonitrile in a mobile phase of acetonitrile and phosphoric buffer in water with subsequent UV detection (215 nm) under a flow of 0.30 ml/min with a sample injection volume of 2-3 µl. Purity was evaluated as the area of the main peak divided by the area of all peaks×100%.

The stability of formulations presented in table 15 measured as % purity of total Compound 1 with RP-UHPLC.

The results confirm an increased chemical stability of Compound 1 in the combo-formulations when zinc is decreased from 4.5 Zn++/six insulins to 2.4, 2.2 and 2.0 Zn++/six insulins (Table 15, FIG. 8). A change in preservative system from 25/25 mM phenol/m-cresol to 60 mM phenol and 0 m-cresol results in an additional improvement in chemical stability of Compound 1 in combo-formulation.

TABLE 15

Purity of Compound 1 in combo-formulation

| Combo-Formulation | Purity with storage time at 37° C. (weeks) | | | |
|---|---|---|---|---|
|  | 0 | 2 | 4 | 6 |
| I | 97.5% | 96.1% | 94.4% | 92.9% |
| II | 97.6% | 96.6% | 95.8% | 95.0% |

TABLE 15-continued

Purity of Compound 1 in combo-formulation

| Combo-Formulation | Purity with storage time at 37° C. (weeks) | | | |
|---|---|---|---|---|
| | 0 | 2 | 4 | 6 |
| III | 97.6% | 96.7% | 95.9% | 95.2% |
| IV | 97.2% | 96.4% | 95.4% | 94.4% |
| V | 97.3% | 96.6% | 95.9% | 95.1% |
| VI | 97.3% | 96.6% | 95.9% | 95.2% |

Conclusion

When co-formulating Compound 1 with semaglutide in a formulation according to the invention, the chemical stability of Compound 1 increases, compared to using prior art formulation (Formulation I) for combo-formulation of Compound 1 and semaglutide.

Example 7

PK Properties of Co-Formulations with Semaglutide in LYD Pig PK Model

Of the formulations produced in Example 6, Compound 1 reference mono formulation and Combo 1 and combo 2 were characterized in the LYD pig PK animal model. It is important that the PK parameters $t_{max}$ and $t_{1/2}$ of Compound 1, as well as mean residence time (MRT) of Compound 1 were not significantly altered upon co-formulation with semaglutide.

A cross-over study with 16 animals (n=8 for each formulation) was conducted.

TABLE 16

PK parameters of Compound 1

| | Mono reference 1 | Combo 1 | Combo 2 |
|---|---|---|---|
| $t_{max}$ (hr) | 13.0 ± 7.0 | 9.0 ± 2.0 | 8.0 ± 2.0 |
| $t_{1/2}$ (hr) | 48.0 ± 4.1 | 48.6 ± 3.2 | 47.9 ± 5.3 |
| MRT (hr) | 71 ± 6 | 69.0 ± 4.0 | 68.0 ± 4.0 |

Average values±standard deviation are shown.

The PK parameters for Compound 1 when co-formulated with semaglutide in Combo 1 and Combo 2 were not significantly changed compared to Compound 1 administrated as a mono-formulation. The $t_{max}$ values were slightly lower for the co-formulations, but with the standard deviation for the Compound 1 reference the values are overlapping. The $t_{1/2}$ and MRT were very similar for Compound 1 in the co-formulations compared to the reference mono-formulation. In conclusion the PK properties of Compound 1 were not significantly impacted by the co-formulation with semaglutide.

Example 8

Improved Oligomer Size of Buffer Exchanged Co-Formulations 60/0

The oligomerisation of combo formulations I-VI formed at simulated injection site conditions of Compound 1 was determined according to the protocol described in Example 1. The results are show in in Table 17 and FIG. 9A and FIG. 9B.

TABLE 17

Oligomer size of combo-formulations

| | Combo I | Combo II | Combo III | Combo IV | Combo V | Combo VI |
|---|---|---|---|---|---|---|
| Rh(avg) [nm] | 13.7 | 4.1 | 4.0 | 4.6 | 4.5 | 4.7 |
| S*(avg) [S] | 8.32 | 4.30 | 4.40 | 4.72 | 4.67 | 4.96 |

Conclusion

These experiments show that the size of the oligomers formed at simulated injection site conditions are highly dependent on the zinc content.

The average size of oligomers formed from combo-formulations at simulated injection site conditions is significantly reduced in formulations with low level of zinc (e.g., 2.4 and 2.2 Zn++/six insulins) compared to formulations with high level zinc (e.g. 4.5 Zn++/six insulin). Increasing the level of phenol and decreasing the level of m-cresol further reduce the average size of oligomers formed from combo-formulations at simulated injection site conditions.

The invention claimed is:

1. A pharmaceutical composition comprising A14E, B16H, B25H, B29K((N$^\varepsilon$-Eicosanedioyl-γGlu-[2-(2-{2-[2-(2-aminoethoxy)ethoxy] acetylamino}ethoxy)ethoxy]-acetyl)), desB30 human insulin (Compound 1), from about 1 to about 2% (weight/weight) glycerol; from about 45 to about 75 mM phenol; from about 0 to about 19 mM m-cresol; from about 1.5 to about 2.5 moles of zinc ions per six moles of Compound 1; less than about 25 mM sodium chloride; and having a pH value in the range of from 7.2 to 8.0.

2. The pharmaceutical composition of claim 1, wherein the amount of Compound 1 is in the range of from about 3.5 to about 5.0 mM.

3. The pharmaceutical composition of claim 1, comprising from about 2.0 to about 2.5 moles of zinc ions per six moles of Compound 1.

4. The pharmaceutical composition of claim 1, comprising about 60 mM of phenol and about 10 mM of m-cresol.

5. The pharmaceutical composition of claim 1, comprising about 60 mM of phenol and about 0 mM of m-cresol.

6. The pharmaceutical composition of claim 1, comprising
    from about 4.0 to about 4.5 mM Compound 1;
    from about 1 to about 2% (weight/weight) glycerol;
    from about 50 to about 70 mM phenol;
    from about 0 to about 15 mM m-cresol;
    from about 2.0 to about 2.5 moles of zinc ions per six moles of Compound 1;
    no more than about 25 mM sodium chloride; and
    having a pH value in the range of from 7.2 to 7.6.

7. A method of treating a metabolic disorder, comprising administering the pharmaceutical composition according to claim 6 to a subject in need thereof.

8. The pharmaceutical composition of claim 1, comprising
    about 4.2 mM Compound 1;
    about 1.5% (weight/weight) glycerol;
    about 60 mM phenol;
    about 0 mM m-cresol;
    about 2.2 moles of zinc ions per six moles of Compound 1;
    about 20 mM sodium chloride; and
    having a pH value of about 7.4.

9. A method of treating a metabolic disorder, comprising administering the pharmaceutical composition according to claim 8 to a subject in need thereof.

10. The pharmaceutical composition of claim 1, comprising about 4.2 mM Compound 1; about 1.5% (weight/weight) glycerol; about 60 mM phenol; about 10 mM m-cresol; about 2.2 moles of zinc ions per six moles of compound 1; about 20 mM sodium chloride; and having a pH value of about 7.4.

11. A method of treating a metabolic disorder, comprising administering the pharmaceutical composition according to claim 10 to a subject in need thereof.

12. A method of treating a metabolic disorder, comprising administering the pharmaceutical composition according to claim 1 to a subject in need thereof.

* * * * *